United States Patent
Appaiah et al.

(10) Patent No.: US 10,092,608 B2
(45) Date of Patent: *Oct. 9, 2018

(54) REDUCING CONJUGATIVE PLASMIDS IN BACTERIA

(71) Applicant: GangaGen, Inc., Palo Alto, CA (US)

(72) Inventors: C. B. Appaiah, Bangalore (IN); Jayasheela Manur, Bangalore (IN); Bharathi Sriram, Bangalore (IN)

(73) Assignee: GangaGen, Inc., Newark, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/948,730

(22) Filed: Nov. 23, 2015

(65) Prior Publication Data

US 2016/0310549 A1 Oct. 27, 2016

Related U.S. Application Data

(63) Continuation of application No. 12/922,114, filed as application No. PCT/US2009/036620 on Mar. 10, 2009, now Pat. No. 9,193,946.

(60) Provisional application No. 61/035,304, filed on Mar. 10, 2008.

(51) Int. Cl.
| | |
|---|---|
| *C12N 15/00* | (2006.01) |
| *A61K 35/76* | (2015.01) |
| *C12N 1/20* | (2006.01) |
| *A01N 63/00* | (2006.01) |
| *C07K 14/005* | (2006.01) |
| *C12N 15/74* | (2006.01) |

(52) U.S. Cl.
CPC .............. *A61K 35/76* (2013.01); *A01N 63/00* (2013.01); *C07K 14/005* (2013.01); *C12N 1/20* (2013.01); *C12N 15/74* (2013.01)

(58) Field of Classification Search
None
See application file for complete search history.

(56) References Cited

U.S. PATENT DOCUMENTS

| | | |
|---|---|---|
| 5,389,531 A | 2/1995 | Junetsu et al. |
| 6,482,647 B1 | 11/2002 | Stemmer |

OTHER PUBLICATIONS

Alcamo, Fundamentals of Microbiology, Jones and Bartlett Publishers, 6$^{th}$ ed., p. 342 (2001).

(Continued)

*Primary Examiner* — Jennifer E Graser
(74) *Attorney, Agent, or Firm* — Kilpatrick Townsend & Stockton LLP

(57) ABSTRACT

The present invention provides methods and compositions to reduce prevalence of plasmids in microbial colonies, including infections, and includes therapeutic compositions, methods for treatment of infections, and methods for identifying additional such compositions. Means are provided to reduce the copy numbers of antibiotic resistance genes, and to confer phage binding to cells lacking receptors for those phage.

9 Claims, No Drawings

(56) References Cited

OTHER PUBLICATIONS

Calendar, The Bacterophages, Oxford University Press, 2$^{nd}$ ed., pp. 235-236, pp. 268, pp. 303, pp. 334, pp. 351, pp. 457, pp. 412 (2006).
Grahn et al., "Assembly of a functional phage PRD1 receptor depends on 11 genes of the IncP plasmid mating pair formation complex," 1997, Journal of Bacteriology, Vo. 179, No. 15, pp. 4733-4740.
Jalasvuori et al., 2011, "Bacteriophage selection against a plasmid-encoded sex apparatus leads to the loss of antibiotic-resistatnce plasmids", Biology Letters, 7(6):902-905. ePub Jun. 1, 2011.
Mindich et al., 1976, "Isolation of nonsense suppressor mutants in Pseudomonas", Journal of Bacteriology, 126(1):177-182.
Schroder et al., "The mating pair formation system of conjugative plasmids—A versatile secretion machinery for transfer of proteins and DNA,".
O'Flaherty et al., "Bacteriophage and their lysins for elimination of infectious bacteria," 2009, FEMS Microbiology Reviews, vol. 33, No. 4, 801-819.
Smit et al., "Self-Transmissible Mercury Resistance Plasmid with Gene-Mobilizing Capacity in Soil Bacterial Population: Influence of Wheat Roots and Mercury Addition", *Applied and Environmental Microbiology*, vol. 64, No. 4, pp. 1210-1219 (1998).
Rakhuba et al., "Bacteriophage Receptors, Mechanisms of Phage Adsorption and Penetration into Host Cell", *Polish Journal of Microbiology*, vol. 59, No. 3, pp. 145-155 (2010).
Xu et al., "The receptor binding protein P2 of PRD1, a virus targeting antibiotic-resistant bacteria, has a novel fold suggesting multiple functions," 2003, Structure, vol. 11, No. 3, pp. 309-322.
Office Action from CN Appl. No. 200980116840.1, dated Apr. 1, 2012 (English Translation version).
Office Action from CN Appl. No. 200980116840.1, dated Jan. 21, 2013 (English Translation version).
Office Action from CN Appl. No. 200980116840.1, dated Feb. 19, 2014 (English Translation version).
Office Action from EP Appl. No. 09719220.7, dated May 21, 2012.
Office Action from JP Appl. No. 2010-550806, dated Nov. 6, 2013 (English Translation version).
Office Action from MX Appl. No. a/2010/009934, dated Mar. 13, 203 (English Translation version).
International Search Report dated Oct. 23, 2009, issued in related International PCT/US2009/036620, filed Mar. 10, 2009.
Olsen, et al. "Characteristics and purification of PRR1, an RNA phage specific for the broad host range Pseudomonas R1822 drug resistance plasmid." Journal of virology 12, No. 6 (1973): 1560-1567.
Olsen, et al. "Characteristics of PRD1, a plasmid-dependent broad host range DNA bacteriophage." Journal of virology 14, No. 3 (1974): 689-699.
Olsen, et al. "Host range and properties of the Pseudomonas aeruginosa R factor R1822." Journal of Bacteriology 113, No. 2 (1973): 772-780.

REDUCING CONJUGATIVE PLASMIDS IN BACTERIA

CROSS-REFERENCES TO RELATED APPLICATIONS

The present application is the continuation application of U.S. application Ser. No. 12/922,114, filed Sep. 10, 2010, which is the U.S. National Stage entry of International Application No. PCT/US2009/036620, filed Mar. 10, 2009 and claims priority to U.S. Application No. 61/035,304, filed Mar. 10, 2008.

FIELD OF THE INVENTION

The present invention provides methods and compositions to reduce numerical or mass amounts of various plasmids found in microbial colonies, including bacterial infections, and includes compositions, methods for treating of colonies, and methods for identifying additional such compositions. In various embodiments, the invention provides for significantly reducing the prevalence of antibiotic resistance markers harbored in a target bacterial culture.

BACKGROUND OF THE INVENTION

Bacteria are ubiquitous, and are found in previously considered uninhabitable environments. They are common and diverse ecologically, and find unusual and common niches for survival. They are present throughout the environment, and are present in soil, dust, water, and on virtually all natural surfaces. Many are normal and beneficial bacterial strains, which provide a synergistic relationship with hosts. Others are not so beneficial, or cause problems along with benefits under specific conditions.

Pathogenic bacteria can cause infectious diseases or significant symptoms in humans, in other animals, and also in plants. Some bacteria can only affect particular hosts; others cause trouble in a number of hosts, depending on host specificity of the bacteria. Others may be innocuous or dormant in certain circumstances, and can emerge as problems in other contexts or situations. Diseases caused by bacteria, whether alone or in combinations, are almost as diverse as the bacteria themselves and include food poisoning, tooth decay, anthrax, general infectious diseases, and even certain forms of cancer. These clinical issues are typically the subject of the field of clinical microbiology.

Bacteria are natural targets of certain viruses, e.g., bacteriophage, or phage. Phages have evolved on their natural hosts, and have a very fast rate of replication and evolution. Phage can capitalize on the least vulnerability presented by the physiology or biology of their hosts. As such, appropriate harnessing of phage structure, physiology, and principles should be useful to minimize or control bacteriological caused problems.

Certain bacteria are normally innocuous, but become pathogenic upon presentation of the appropriate opportunity, or become problematic upon introduction to an abnormal site or situation. Moreover, certain bacterial combinations evolve together and may operate synergistically to complement functions lacking in individual members of a colony. However, many assorted mechanisms exist, e.g., in a multicellular organism, to handle different amounts of bacteriological challenge, and the complete eradication of the bacterial cultures is often not necessary. In many cases, incomplete eradication of the bacterial population will decrease the effects of infection to allow the system to resolve problems by alternative mechanisms, e.g., the immune system.

Statistically, infectious diseases are a major medical problem. See, e.g., Watstein and Jovanovic (2003) *Statistical Handbook on Infectious Diseases* Greenwood, ISBN: 1573563757. In the U.S., some 40-70K deaths result from bloodstream nosocomial (hospital derived) infections each year.

In particular, antibiotics have revolutionized clinical medicine over the last half century. Since the original discovery of antibiotic phenomena, the mechanism of action and development of this class of remarkable therapeutic entities has made enormous progress. See, e.g., Therrien and Levesque (2000) *FEMS Microbiol. Rev.* 24:251-62; Durgess (1999) *Chest* 115(3 Suppl):19S-23S; Medeiros (1997) *Clin. Infect. Dis.* 24(Suppl 1):519-45; Jones (1996) *Am. J. Med.* 100(6A):3S-12S; Ford and Hait (1993) *Cytotechnology* 12:171-212; and Liu (1992) *Compr. Ther.* 18:35-42. Antibiotics had about $32B worldwide sales in 2002.

The widespread appearance of antibiotic-resistant bacteria has emphasized the vulnerability of current antimicrobial treatments to bacterial adaptation. See, e.g., Wise (2007) "An overview of the Specialist Advisory Committee on Antimicrobial Resistance (SACAR)" *J. Antimicrob. Chemother.* 60 Suppl 1:i5-7. PMID: 17656382; Finch (2007) "Innovation—drugs and diagnostics" *J. Antimicrob. Chemother.* 60 Suppl 1:i79-82, PMID: 17656390; Walsh (1992) *Antibiotics: Actions, Origins, Resistance* Amer. Soc. Microbiol., ISBN: 1555812546; Cunha (1992) *Antibiotic Essentials* Physicians Press, ISBN: 1890114413; Amyes (2003) *Magic Bullets, Lost Horizons: The Rise and Fall of Antibiotics* Taylor & Francis, ISBN: 0415272033; Axelsen (2001) *Essentials of Antimicrobial Pharmacology: A Guide to Fundamentals for Practice* Humana Press, ISBN: 0896038424; and Mainous and Pomeroy (eds. 2001) *Management of Antimicrobials in Infectious Diseases: Impact of Antibiotic Resistance* Humana Press, ISBN: 0896038211.

In addition, mechanisms of antibiotic resistance develop under minimally selective conditions (e.g., at low concentration of antibiotic), and these mechanisms are often transferred between hosts. Thus, mechanisms evolve in different organisms, and often are introduced into new hosts, where these same mechanisms are further refined and optimized. Often combinations of mechanisms are generated, genetically linked together, and are transferred together among bacterial hosts. These combinations often result in genetic clustering of DNA segments encoding linked multiple drug resistance markers Thus, improved methods for decreasing prevalence of resistance encoding plasmids, growth, or survival or for limiting bacterial virulence or pathogenicity will find great utility. This utility may be applicable to environmental, local, topical, or particularly in vivo colonization. The present invention addresses these and other significant problems.

BRIEF SUMMARY OF THE INVENTION

The present invention is based, in part, upon the realization that there exist various broad host range phage which can infect many different hosts. See, e.g., Grahn, et al. (2006) "PRD1: Dissecting the Genome, Structure and Entry" in Calendar (ed.) *The Bacteriophages* (2d ed.) Oxford Univ. Press, ISBN-13: 9780195148503. The PRD1 is an exemplary member of the genus Tectiviridae, which is structurally and functionally defined. However, the classification scheme is evolving and the similarity of the phage to higher animal adenovirus functions is recognized. This indicates that certain fundamental structural features are shared, which these phages utilize to achieve a common goal of infecting and replicating in a wide variety of host bacterial species. In particular, these broad host ranges span across the Gram-negative and Gram-positive distinction, suggesting that certain structural features are shared in the binding and infection processes. Many genetic elements which encode mechanisms of antibiotic resistance also can contain the means for vulnerability of cells containing those genetic elements. For example, certain bacterial plasmids which encode antibiotic resistance genes also encode a receptor which makes the host cell vulnerable to binding (and killing) by a bacteriophage. Alternatively, the plasmid may encode genes or structures which may be transferred into cells otherwise lacking the plasmid, thereby resulting in transfer of resistance genes and linked vulnerability markers. This mechanism can serve as a means for horizontal transmission of the resistance or virulence encoding plasmid to similar hosts lacking the resistance marker(s). If the vulnerability genes are also transferred, these hosts then become sensitive to means for elimination.

The present invention provides means to effectively target cells containing certain genetic elements, particularly transmissible forms, encoding antibiotic resistance or virulence. In other embodiments, it provides means to transfer phage binding and/or killing susceptibility to a wide variety of target host bacteria.

The present invention provides methods to decrease the prevalence of a conjugative plasmid encoding a phage, e.g, tectivirus, receptor within a heterogeneous bacterial culture. The methods use a biological system (exemplified by a phage or a part thereof) dependent upon bacterial mating pair formation system (exemplified by conjugative pili or a part thereof) for its antibacterial activity (elimination/reduction in the number of bacteria harboring undesirable properties like antibiotic resistance, virulence etc) to target cells containing the genetic elements.

As an optional first step, a host bacteria that includes the conjugative plasmid and expresses the phage receptor is produced by exposing the bacterial culture to a mating pair formation system that provides transfer of the conjugative plasmid that encodes the phage receptor from a donor member to a recipient member of said bacterial culture and allowing said system to effect transfer of said conjugative plasmid from said donor member to said recipient member of said bacterial culture. As a second step (or first step, if the previous step is not carried out), once the host cells that express the phage receptor are present, the bacterial culture is exposed to an appropriate phage that binds the receptor. As part of its life cycle, the phage kills the host bacteria, thus, decreasing the prevalence of the conjugative plasmid encoding the phage receptor within the heterogeneous bacterial culture.

In one embodiment, the decrease in prevalence is a decrease in relative or absolute number of said conjugative plasmid in said bacterial culture; or a decrease in relative or absolute number of said conjugative plasmid per member of said bacterial culture, or a decrease in the relative or absolute number of said plasmid containing hosts found in the heterogeneous bacterial culture. In a further embodiment, the decrease in prevalence is at least two fold less than the prevalence before exposure to the mating pair system.

In one embodiment, the phage is, e.g., a broad host range lipid-containing phage, including a tectivirus; a member of the PRD1 phage group; a plasmid-dependent broad host range bacteriophage; a tectiviridae, a phage characterized by at least one or more of an icosahedral morphology, lipid content, 55-65 nm diameter head, and a 12-130 nm tail; or is selected from the group of phages designated PRD1, PRR1, PR3, PR4, PR5, L17, PR772, GIL01, pGIL01, BAM35, or GIL16.

In one embodiment, the conjugative plasmid, e.g., is selected from incompatibility groups N, P, or W plasmids; encodes one or more additional protein important in phage replication, (e.g., a protein that functions is binding, infection, replication, or lysis on the plasmid); encodes one or more antibiotic resistance, selection, or virulence markers; is in the form of a separate DNA from a chromosome of said member; or encodes one or more pilus genes.

In one embodiment, the heterogeneous bacterial culture is, e.g., in a logarithmic growth stage; in a steady state growth stage; a *lactobacillus* or dairy product processing culture; in a water treatment facility; in a eukaryotic cell or organ culture; in a eukaryotic host; in or on a vertebrate organism; or in or on a mammal.

In one embodiment, the mating pair formation system includes, e.g., at least one pilus conjugation gene; or another mobilizable element transfer system, such as transduction or electroporation. Alternative systems for introducing appropriate plasmids include phage-based DNA delivery systems.

In further embodiments, the transfer of genetic material is, e.g., at a temperature of at least 30° C.; at a temperature wherein a plurality of pilus genes are expressed. Another condition that can be varied is time of transfer, e.g., between two and twelve hours or more preferably two hours. In one embodiment, the donor cell is an F+ bacteria cell. In another embodiment, the recipient cell is an F− bacteria cell. In a preferred embodiment, the transfer of genetic material results in an increase in the members of said bacterial culture comprising said conjugative plasmid. In another preferred embodiment, the ration of donor cell to recipient cell is within two log units of 1:1, e.g., 100:1 to 1:100.

Regarding the addition of tectivirus phage to the heterogeneous bacterial culture, in one embodiment, at least 10 phage are added for each bacterial cell comprising said conjugative plasmid encoding said receptor, i.e., for each cell that is susceptible to infection by the phage, including a tectivirus. In one embodiment, the phage decreases the number of said conjugative plasmid. In another embodiment, the phage is incapable of replicating in the host bacterium, e.g., due to defective infection, replication, or lysis, including an incompatibility mechanism, including host cells that comprise the conjugative plasmid. In a further embodiment, the phage cannot replicate its genome in host bacteria comprising said conjugative plasmid Thus, phage that are replication competent in the host bacterium are not required for the methods of the invention.

In one aspect the invention provides a method to transfer a mobilizable genetic element that confers susceptibility to attachment by a phage, e.g., a tectivirus, within a heterogeneous bacterial culture. The heterogeneous bacterial culture includes a donor bacteria cell susceptible to phage binding and a recipient bacteria cell that is not susceptible to phage binding. The transfer of the genetic element occurs between the donor bacterial cell and the recipient bacterial cell under appropriate conditions. With the transfer of the genetic element to the recipient bacterial cell, the recipient bacterial cell becomes susceptible to binding by a phage typically leading to the death of the recipient cell.

The mobilizable element is a typically plasmid encoding, e.g., a tectivirus phage receptor gene or a pilus gene. The plasmid can be selected from any of the following plasmids:

F, R386, R1, Col B-K99, Col B-K166, R124, R62, R64, R483, R391, R46, R724, RP4, RK2, R751, RSF1010, R401, R388, or S-a; in an Inc group N, P, or W; or in an Inc group D, M, X, P1, U, C, or J.

Examples of donor bacterial cells susceptible to the tectivirus phage are, e.g., an F+ cell; from a Gram-negative bacterial specie; from a genus such as *Escherichia, Pseudomonas, Salmonella, Proteus, Vibrio, Acinetobacter, Bacillus,* or *Micrococcus*

Examples of recipient bacterial cells are an F- cell; from a Gram-negative bacterial specie; from a genus such as *Escherichia, Pseudomonas, Salmonella, Proteus, Vibrio, Acinetobacter, Bacillus,* or *Micrococcus*; or a carrier of an antibiotic resistance gene or a virulence gene;

Examples of tectivirus phage include PRD1, AP50, Bam35, NS11, PR3, PR4, PR5, PR722, L17, or P37-14.

In one embodiment, the donor bacterial cell and said recipient bacterial cell are from different bacterial species or different bacterial genera.

In a further embodiment, the method includes a step of administering a phage, e.g., tectivirus, to infect receptor-expressing, phage-susceptible host cells resulting in death of the susceptible host cells or a decrease in the number of mobilizable elements encoding antibiotic resistance or bacterial virulence genes in the heterologous bacterial culture. Antibiotics can also be administered with the phage, e.g., sequential or concurrent administration.

In one aspect the invention provides a recombinant genetic construct that includes a nucleic acid encoding a phage, e.g., tectivirus, receptor component. Expression of the phage receptor component can be driven by a strong heterologous promoter that is functional in the host bacterial cell. In one preferred embodiment, the promoter is an inducible promoter that can drive expression of the receptor gene to levels at least 2, 4, 5, 10 or more times higher in the induced state as compared to the induced state. The recombinant genetic construct can also include a selectable marker that is linked to the nucleic acid encoding the tectivirus receptor. The host bacterium can be, e.g., a Gram-negative bacterium.

In another aspect the invention provides a pharmaceutical composition comprising a transmissible DNA encoding a phage receptor which binds to a lytic phage, wherein the lytic phage will kill a bacterial cell expressing the phage receptor, and a pharmaceutically acceptable excipient. In certain embodiments, the transmissible DNA is an Inc plasmid selected from N, P, W, D, M, X, P1, U, W, C, or J; or the lytic phage is a phage designated PRD1, PRR1, PR3, PR4, PR5, L17, PR772, GIL01, pGIL01, BAM35, or GIL16. Further provided is a kit comprising one or more compartments with the lytic phage and the pharmaceutical composition.

The present invention provides a method to decrease the prevalence of a conjugative plasmid encoding antibiotic resistance and/or virulence factor in a heterogeneous bacterial population. The method comprises the steps of contacting the heterogeneous bacterial population with phage, e.g., a Tectivirus, that binds to or enters a bacterial host cell harboring the conjugative plasmid via an interaction with a receptor protein encoded by a nucleic acid component of the conjugative plasmid. Once the phage has contacted and inserts its genome into the bacterial host cell, the host cell can express the appropriate receptor. A phage which binds that receptor can kill or reduce replication of the host bacterial cell and the relevant plasmid contained therein. In a further aspect the method includes a step of transforming an increased proportion of the bacterial population with the plasmid that encodes an antibiotic resistance and/or virulence factor and a phage receptor. Thus, an infectious or pathogenic bacterial population can be converted to a bacterial population that is susceptible to killing or reduction in proliferation after infection by the appropriate phage.

In one embodiment, the absolute number of such plasmid harboring bacteria in the heterogeneous bacterial population decrease, e.g., by 10%, 20%, 25%, 40%, 50%, 75%, 80%, or 90% of the starting total. The number of bacteria present can be determined by, e.g., cell counting using a hemocytometer or by serial dilution onto an appropriate medium, including under appropriate selection conditions.

In another embodiment, the phage is a broad host range phage. Examples of broad host range phages include the Tectiviridae family of bacteriophages; plasmid-dependent broad host range bacteriophages; phages characterized by at least one or more of an icosahedral morphology, lipid content, 55-65 nm diameter head; and a 12-130 nm tail; and phages selected from the following group: PRD1, PRR1, PR3, PR4, PR5, L17, PR772, GIL01, Bam35, PhiNS11 or GIL16, AP50, P23-62, -65, -65H, -71, -72, -77, P37-2, -4, -4A, -4B, -6, -6A, -7A, -8, -8B, -9, -9A, -3, -13B, -13C, -13L, -14A, -21, -21C, -21T, -26, -26S, -28, -36, -41, -41A, -41B, -43, -45, -50, -50L, -61, 61L, -62, -63, -64, -64C, -64L, -64T, -71, -72, -72L, -73, -74, -76, -77, -81, -82, -83, -84, -87, -88, P78-76.

In another embodiment, the conjugative plasmid has one or more of the following features: membership in an incompatibility group, e.g., N, P, W, L/M, T, U, W, Y, B/O, FII, I1, K, com9, FI, HI1, HI2, X, A/C, D, FIV, FV/FO, FVI, H13, HII, I2, Igamma, J, V and the like, including variants thereof, e.g., exhibiting substantial sequence or functional relationship; encodes one or more additional genes important in tectivirus phage replication; encodes one or more antibiotic resistance, selection, or virulence markers; is in the form of a separate DNA from the chromosome of the host bacterial cell; or part of the chromosome; encodes one or more pilus genes for bacterial conjugation.

In another embodiment, the heterogeneous bacterial population is in a logarithmic or steady state growth stage. The bacterial population can be found in a variety of environments, e.g., a food processing unit; or in a water treatment facility; a Sewage treatment plant; in a health care unit; in the environment such as a marine environment, estuarine waters, or a hot springs. The bacterial population may be in a synergistic colony where different species interact to make a viable colony, as in a biofilm or the gut of termites. In such colonies, elimination of a critical member may eliminate viability of the population The bacterial population can be found in a eukaryotic cell or organ culture. In a further embodiment, the bacterial population is found in, e.g., a eukaryotic host; in or on a vertebrate organism; or in or on a mammal.

In another embodiment, contact between the bacterial host cell and the phage occurs at a conjugation complex on the bacterial cell surface or on an appendage of the bacterial cell, such as a pilus. The conjugation complex can be associated with either conjugative or mobilizable plasmids. Contact can also occur via a bacteriophage-associated protein that recognizes and binds to the above conjugation complex. For contact between the phage and the host bacterial cell, 37° C. is a preferred temperature, although contact will occur at other lower or higher temperatures. A preferred pH optimum for contact is 7.0, but contact will occur at higher or lower pH values.

In another embodiment, contact between the bacterial host cell and the phage occurs using a phage that is capable of binding to the host bacterial cell at various multiplicities of infection with or without phage amplification.

In another aspect, the invention provides a method to transfer phage binding susceptibility encoded in a transmissible genetic element from a donor bacteria cell susceptible to phage binding to a recipient bacteria cell that is non-susceptible to said phage binding. The method includes a step of exposing the non-susceptible bacterial cell to the susceptible cell, under conditions where the transmissible genetic element is transferred from the donor cell to the recipient cell.

In one embodiment, the transmissible genetic element is a plasmid or chromosomal fragment. The transmissible genetic element preferably encodes a tectivirus phage receptor; or a pilus; or a component of the bacterial conjugation complex. In a further embodiment the transmissible genetic element is a plasmid. Preferred examples of plasmids include, e.g., F, R386, R1, Col B-K99, Col B-K166, R124, R62, R64, R483, R391, R46, R724, RP4, RK2, R751, RSF1010, R401, R388, or S-a. The plasmid can be in an incompatability group (Inc group) such as, N, P, W, L/M, T, U, W, Y, B/O, FII, I1, K, com9, FI, HI1, HI2, X, A/C, D, FIV, FV/FO, FVI, H13, HII, I2, Igamma, J, and V, or variants thereof. The phage-susceptible donor can be, e.g., an F+ cell; or from a genus such as *Escherichia, Pseudomonas, Salmonella, Proteus, Vibrio, Acinetobacter, Staphylococcus, Streptococcus, Bacillus*, or *Micrococcus*; or a carrier of an antibiotic resistance gene or a virulence gene. The non-phage-susceptible recipient bacterial cell can be e.g., an F− cell; or from a genus such as *Escherichia, Pseudomonas, Salmonella, Proteus, Vibrio, Acinetobacter, Staphylococcus, Streptococcus, Bacillus*, or *Micrococcus*. If a tectivirus phage is used in the method, preferred tectivirus include, e.g., PRD1, PRR1, PR3, PR4, PR5, L17, PR772, GIL01, Bam35, PhiNS11 or GIL16, AP50, P23-62, -65, -65H, -71, -72, -77, P37-2, -4, -4A, -4B, -6, -6A, -7A, -8, -8B, -9, -9A, -3, -13B, -13C, -13L, -14A, -21, -21C, -21T, -26, -26S, -28, -36, -41, -41A, -41B, -43, -45, -50, -50L, -61, 61L, -62, -63, -64, -64C, -64L, -64T, -71, -72, -72L, -73, -74, -76, -77, -81, -82, -83, -84, -87, -88, P78-76. In a preferred embodiment, the proportion of tectivirus phage susceptible cells increases in the bacterial colony or infection.

In another embodiment, a phage, e.g., tectivirus is used to infect cells made to express receptor, and the following results preferably occur: the phage infection results in death of the susceptible cells; transmission of other mobilizable elements encoding antibiotic resistance or bacterial virulence genes is decreased in the susceptible cell population; the antibiotic and phage-resistant and virulent bacterial population decreases.

In another aspect of the invention, appropriate antibiotic/s are administered with the phage in any of the methods described above. In a preferred embodiment, the combined administration of the phage and antibiotic results in a synergistic reduction in susceptible bacterial cells in the heterogeneous bacterial population or in reduction of the number of plasmid DNA copies found in the population.

DETAILED DESCRIPTION OF THE INVENTION

I. Introduction

A peculiar group of phages isolated from diverse parts of the world have been characterized to infect Gram-negative bacteria harboring a conjugative plasmid. See Grahn, et al. (2006) "PRD1: Dissecting the Genome, Structure and Entry" in Calendar (ed.) *The Bacteriophages* (2d ed.) Oxford Univ. Press, ISBN-13: 9780195148503. Very similar isolates also infect Gram-positive host bacteria. These closely related phages have been classified together into the family Tectiviridae and include, e.g., the phages designated PR3, PR4, PR5, PR772, L17, AP50, NS11, and P37-14. Among various interesting features of these phages is that the replication mechanism, capsid architecture, major coat protein fold, and vertex structure strongly resemble those of human adenovirus. This has led to a suggestion that these viruses belong to an original lineage having a common ancestor that precedes the divergence of the bacterial and eukaryotic domains of life. Structural features of the Tectiviridae (referred to hereafter as tectiviruses) suggest some underlying principles consistent with these phages possessing binding and infection mechanisms which are functionally applicable to both Gram-negative and Gram-positive host bacteria. Thus, general phage biology dogma regarding high selectivity in host binding and infection seems to be inapplicable to these particular broad host range phage, and perhaps to others, as described.

The tectiviruses typically possess an icosahedral outer protein capsid, a lipid membrane bilayer, and the viral DNA genome. The best characterized PRD1 phage member possesses a broad host range, is a donor-specific phage, and infects only host cells that carry IncP, IncN, or IncW, which are multiple drug resistance conjugative plasmids. The Inc plasmids are "incompatibility" group plasmids which effectively prevent other plasmids of the same incompatibility group to share the host, but seem to be necessary for the phage to infect. Thus, the plasmids seem to encode some function necessary for the phage to infect, presumptively the phage receptor. Different incompatibility group plasmids appear to be able to coexist in a single host but a mechanism exists to prevent multiple plasmids of the same group to coinfect a single host. The plasmids typically encode phage receptors, and confer phage binding (and ultimately infection) susceptibility onto the host bacterium. This implies that susceptibility may be transferred to host cells which are initially not susceptible.

Many different Inc groups exist, with one or more described plasmids in the group. For example, the group F1 is represented by plasmids F and R386; group FII represented by the plasmid R1; group FIII represented by the plasmids Col B-K99 and Col B-K166; group FIV represented by the plasmid R124; group I represented by the plasmids R62, R64, and R483 (at least 5 subgroups); group J represented by the plasmid R391; group N represented by the plasmid R46; group O represented by the plasmid R724; group P represented by the plasmids RP4, RK2, and R751; group Q represented by the plasmid RSF1010; group T represented by the plasmid R401; and group W represented by the plasmids R388 and S-a. Other similar groups with fewer representatives exist, and will be identified over time.

II. Definitions

A "bacterial culture" is a population of cells, some or all of which are bacteria. In laboratory contexts, typically the culture is homogeneous, and often clonal. In the clinical context, "heterogeneous bacterial cultures" often exist. The culture will often include multiple bacterial species, each often containing genetic variants, and these can interact and exhibit systems biology effects upon the collective population. A heterogeneous bacterial culture can include more than one bacterial species. In some embodiments, more than two, three, five or ten bacterial species are found in a heterogeneous bacterial culture. Dynamic aspects of the heterogeneous bacterial culture may cause changes in the relative amounts and prevalence of different subpopulations within the culture and the resulting direction of population development. In other contexts, specific isolates may be clonal, and certain subpopulations may be a focus of or cause of different infectious disease symptoms. Different members of the culture may be clonal, may be multiclonal, or the culture may include mixed species. The population may have synergistic populational components, which often form biofilm structures. See, e.g., Talsma (2007) "Biofilms on medical devices" *Home Healthc. Nurse* 25(9):589-94 PMID: 18049256; Paju and Scannapieco "Oral biofilms, periodontitis, and pulmonary infections" *Oral Dis.* 13(6): 508-512 PMID: 17944664; Visai, et al. (2007) "*Staphylococcus* biofilm components as targets for vaccines and drugs" *Int. J. Artif. Organs* 30(9):813-819 PMID: 17918127; del Pozo and Patel (2007) "The challenge of treating biofilm-associated bacterial infections" *Clin. Pharmacol. Ther.* 82(2):204-209 PMID: 17538551; and Ryan (2007) "Infection following soft tissue injury: its role in wound healing" *Curr. Opin. Infect. Dis.* 220(2):124-128 PMID: 17496569, as well as general clinical microbiology textbooks. Heterogeneous bacterial cultures include synergistic/symbiont cultures, such as biofilms. For this type of heterogeneous bactieral culture, elimination of one component of a culture may render the culture inviable, as a whole. See, e.g., Colin and Moran (2006) "Molecular Interactions between Bacterial Symbionts and Their Hosts" *Cell* 126: 453-465.

Examples of typical sites of mammalian bacterial infection and heterogeneous bacterial cultures that are found in the infected are listed below. Any site of infection can include at least two or more of the species listed below.

Human/Animal intestine: *Escherichia* species, *Salmonella* species, *Shigella* species, *Pseudomonas* species, *Klebsiella* species, and *Proteus* species.

Human Throat (and Aspiration pneumonia, nasal sinuses infection, middle ear infection & so on): Staphylococcal species, Streptococcal species, *Haemophilus* species, *Cornybacterium* species, and *Neisseria* species.

Skin wound/burn wound: *Pseudomonas* species, Staphylococcal species, *Klebsiella* species. Road accident wound infection: Mostly soil organisms+anaerobes (*Clostridium* species, bacterioides species).

Heterogeneous bacterial cultures found in the environment can include at least two bacterial species, including one of the following species: *Escherichia* species, *Salmonella* species, *Shigella* species, *Pseudomonas* species, *Klebsiella* species, *Proteus* species, *Bacillus* species, soil mycobacteria, and *Streptomyces*. This list is not exclusive of other types of bacterial species which may be represented in the population.

Plasmid containing subsets or subpopulations may exist, e.g., some bacteria may possess various different plasmids or combinations thereof, which may confer a variety of selective advantages under certain conditions. Certain plasmids may encode one or more antibiotic resistance or virulence genes. The Inc group plasmids typically serve to prevent other plasmids of the incompatibility group from coexisting in the same host. See, e.g., Fernández-López, et al. (2006) "Dynamics of the IncW genetic backbone imply general trends in conjugative plasmid evolution" *FEMS Microbiol. Rev.* 30(6):942-66 PMID: 17026718; and Adamczyk and Jagura-Burdzy (2003) "Spread and survival of promiscuous IncP-1 plasmids" *Acta Biochim. Pol.* 50(2):425-53 PMID: 12833168. Often heterogeneity in a species may reflect lack of selective pressure between different forms, or the incomplete selection of a single preferred phenotype.

Tectiviruses, members of the family Techtiviridae, refer to certain broad host range phage. While tectiviruses are one form of broad host range phage, others do exist, and others will be discovered upon proper characterization or relevant selection criteria. Classification criteria may be based upon combinations of structural and functional features shared among members of the genus or species. In particular, other similar phages exist, e.g., of the Inoviridae, Leviviridae, and Podoviridae categories, whose infectivity is plasmid dependent. In particular, these examples include phage whose host range is defined by the hosts possessing particular plasmids, e.g., which encode a receptor for the respective phage. As such, these plasmids confer the capacity for phage binding and infection of hosts compatible with the plasmid.

Among other plasmid dependent phages include: the IncP plasmid provides susceptibility to certain Inoviridae phages, e.g., PR64FS and If1. As described elsewhere, the IncP, IncN, and IncW provide susceptibility to certain Tectiviridae phages, e.g., PRD1, PR4, PR3, PR5, PR772, and L17. The IncD plasmid provides susceptibility to certain Leviviridae or RNA phage, including, e.g., Phage D; R687, R711b, R778b, and R840; the plasmid encodes structures resembling phage M and pilH alpha and the phage attach to the sides and end of the pili. The plaque formation exhibits some temperature sensitivity often with higher sensitivity at lower temperatures. The IncM provides sensitivity to RNA phages, e.g., phageM, and seems to work on many organisms containing this plasmid. The IncX, IncM, IncN, IncP1, IncU, IncW and the plasmid R775 seem to provide sensitivity to filamentous phage which adsorb to the tips of pili, including, e.g., phageX and R6K. The IncC provides susceptibility to RNA phage, including, e.g., phageC-1; or filamentous phage, including, e.g., phageC-2. The IncC, IncD, and IncJ provide susceptibility to siphoviridae phages, including, e.g., phageJ. The Folac plasmid provides susceptibility to phage Folac. The IncP plasmids also provide susceptibility to the filamentous phage Pf3 (see Luiten, et al. (1985) *J. Virol.* 56(1)268-276), and the receptor binding segments therein can be used to target a killing agent, whether an intact phage or other activity linked to the receptor binding domain (see, e.g., WO 2007/130655; PCT/US2007/010972). Likewise, the IncI or IncN plasmids provide susceptibility to the filamentous phage Ike; and the IncI, IncN, and IncP plasmids confer susceptibility to the filamentous phage 12-2. See, e.g., Bradley, et al. (1983) *J. Bact.* 154(1): 505-507.

Various of the tectiphage described affect different Gram positive organisms, e.g., Bam35 acts on *B. thuringenesis*; AP50 on *B. antracis*; PhiNS1 on *B. adiocalarius*; GIL16 and GIL01 on *B. thuringenesis*; and pBCLIN on *B. cereus*.

Broad host range phage will be phage whose host range is typically broader than the dogma of highly specific bacterial host specificity. See, e.g., Bamford, et al. (1995) "Bacteriophage PRD1: a broad host range DSDNA tectivirus with an internal membrane" *Adv. Virus Res.* 45:281-319 PMID: 7793328; and Saren, et al. (2005) "A snapshot of viral evolution from genome analysis of the tectiviridae family" *J. Mol. Biol.* 350(3):427-40 PMID: 15946683. Typically, the broad host range phage can infect many hosts which express an appropriate receptor molecule but may be from hosts which are classified in divergent genus, family, or order classification categories. The receptor may be encoded on a conjugative plasmid, or elsewhere, so as to provide necessary genes for binding, infection, and/or killing, as desired.

A conjugative plasmid typically encodes the functions needed for its own intercellular transmission, preferably by conjugation. In the context used herein, the function of encoding most of the necessary genes is intended, which leaves the possibility of selecting for or engineering constructs which may complement missing components on the plasmid itself. There are also means to broaden host range of the plasmids by adding or selecting plasmids which already exhibit broad host ranges, including either low specificity origins of replication, or multiple origins compatible with the desired range of hosts. The conjugation plasmid is one form of "mobilizable element", which will typically be the physical means by which diversification of bacterial species and pathotypes is achieved. For example, lateral gene transfer (LGT) of diverse mobile DNA elements can occur by means of plasmids, phages, transposons, and genomic islands. While the most commonly considered means are plasmids, similar functions can be achieved by analogous application of the principles described among phages, transposons, and the like.

Decrease in conjugative plasmids, whether in absolute numbers or prevalence in host cells, may be effected in many ways. The selective disadvantage of carrying a large plasmid may select against hosts possessing the plasmid or cause the hosts to lose all or part of the plasmid. In contrast, the plasmids may confer an advantageous phenotype, e.g., antibiotic resistance, and all of the cells might possess the plasmid. In other situations, the plasmid may encode the receptor for a phage, which makes the phage a means to kill or eliminate hosts possessing the plasmid. In some embodiments, the conjugative plasmid is a recombinant plasmid that has been engineered to decrease its size (decrease the total number of nucleotides), while maintaining the function of the conjugative plasmid, i.e., the ability to transfer between cells and the presence of a nucleic acid sequence that, when expressed in the host cell, encodes a receptor for a tectivirus. The decrease may be in absolute number of plasmids, in the number of relevant hosts in the culture which possess the plasmid, or in the relative fraction of hosts possessing the plasmid.

A mating pair formation system is the means by which DNA is transferred from one cell to another. This is distinct from a cell dividing to produce two cells, but where two cells transfer some component of DNA from one to the other. See, e.g., See, e.g., Schaechter (2004) *The Desk Encyclopedia of Microbiology* (2d ed.) Academic Press, ISBN 0126213615, 9780126213614; Funnell and Phillips (eds. 2004) *Plasmid Biology* ASM Press, ISBN-10: 1555812651, ISBN-13: 978-1555812652; Streips and Yasbin (2003) *Modern Microbial Genetics* (2d ed.) Wiley-IEEE, 2003, ISBN 0471461083, 9780471461081; Schrodera and Lankab (2005) "The mating pair formation system of conjugative plasmids—A versatile secretion machinery for transfer of proteins and DNA" *Plasmid* 54(1):1-25; Francia, et al. (2004) "A classification scheme for mobilization regions of bacterial plasmids" *FEMS Microbiol Rev.* 28(1):79-100; Frost, et al. (1994) "Analysis of the sequence and gene products of the transfer region of the F sex factor" *Microbiol Rev.* 58(2):162-210; Novotny, et al. (1969) "Functions of F Pili in Mating-Pair Formation and Male Bacteriophage Infection Studied by Blending Spectra and Reappearance Kinetics" *J Bact.* 98(3):1307-1319; Delmonte-Corrado, et al. (2007) "Lectin-Binding Sites Involved in Paramecium primaurelia Mating Pair Formation" *Journal of Eukaryotic Microbiology* 44(6):603-608; Murakami and Haga (1995) "Interpecific Pair Formation Induced by Natural Mating Reaction in Paramecium" *Zoological Sci.* 12:219-223. Mating pair formation in Gram-positive Bacteria: Dale and Park (2004) Molecular Genetics of Bacteria (4th ed.) John Wiley and Sons. Typically, the transfer occurs via a conjugation mechanism, but variants thereof, including transformation, phage or partial phage genome transfer, transduction, or other related processes will often achieve the desired purpose. In the conjugation process, the system typically includes the necessary functions for producing pili and which allow for the transfer and use of relevant genetic markers or cassettes, e.g., antibiotic resistance, virulence, or phage receptor markers. Means to supplement or complement incomplete systems exist, e.g., using one or more helper constructs.

"GMP conditions" refers to good manufacturing practices, e.g., as defined by the Food and Drug Administration of the United States Government. Analogous practices and regulations exist in Europe, Japan, and most developed countries.

The term "substantially" in the above definitions of, e.g., "substantially pure", generally means at least about 60%, at least about 70%, at least about 80%, or more preferably at least about 90%, and still more preferably at least about 95% pure, whether protein, nucleic acid, or other structural or other class of molecules.

The practice of this invention can involve the construction of recombinant nucleic acids and the expression of genes in host cells, preferably bacterial host cells. Optimized codon usage for a specific host will often be applicable. Molecular cloning techniques to achieve these ends are known in the art. A wide variety of cloning and in vitro amplification methods suitable for the construction of recombinant nucleic acids such as expression vectors are well known to persons of skill. Examples of these techniques and instructions sufficient to direct persons of skill through many cloning exercises are found in Berger and Kimmel, Guide to Molecular Cloning Techniques, *Methods in Enzymology* volume 152 Academic Press, Inc., San Diego, Calif. (Berger); and *Current Protocols in Molecular Biology*, Ausubel, et al., eds., Current Protocols, a joint venture between Greene Publishing Associates, Inc. and John Wiley & Sons, Inc., (1999 Supplement) (Ausubel). Suitable host cells for expression of the recombinant polypeptides are known to those of skill in the art, and include, for example, prokaryotic cells, such as *E. coli*, and eukaryotic cells including insect, mammalian, and fungal cells (e.g., *Aspergillus niger*).

Examples of protocols sufficient to direct persons of skill through in vitro amplification methods, including the polymerase chain reaction (PCR), the ligase chain reaction (LCR), Qβ-replicase amplification and other RNA polymerase mediated techniques are found in Berger, Sambrook, and Ausubel, as well as Mullis, et al. (1987) U.S. Pat. No. 4,683,202; *PCR Protocols A Guide to Methods and Applications* (Innis, et al. eds) Academic Press Inc. San Diego, Calif. (1990) (Innis); Arnheim and Levinson (Oct. 1, 1990) *C&EN* 36-47; *The Journal Of NIH Research* (1991) 3:81-94; Kwoh, et al. (1989) *Proc. Nat'l Acad. Sci. USA* 86:1173; Guatelli, et al. (1990) *Proc. Nat'l Acad. Sci. USA* 87:1874; Lomell, et al. (1989) *J. Clin. Chem.* 35:1826; Landegren, et al. (1988) *Science* 241:1077-1080; Van Brunt (1990) *Biotechnology* 8:291-294; Wu and Wallace (1989) *Gene* 4:560; and Barringer, et al. (1990) *Gene* 89:117. Improved methods of cloning in vitro amplified nucleic acids are described in Wallace, et al., U.S. Pat. No. 5,426,039.

The term "nucleic acid" refers to a deoxyribonucleotide or ribonucleotide polymer in either single- or double-stranded form, and unless otherwise limited, encompasses known analogues of natural nucleotides that hybridize to nucleic acids in a manner similar to naturally occurring nucleotides. Unless otherwise indicated, a particular nucleic acid sequence includes the complementary sequence thereof.

A "recombinant expression cassette" or simply an "expression cassette" is a nucleic acid construct, generated recombinantly or synthetically, with nucleic acid elements that are capable of affecting expression of a structural gene in hosts compatible with such sequences. Expression cassettes include at least promoters and optionally, transcription termination signals. Typically, the recombinant expression cassette includes a nucleic acid to be transcribed (e.g., a nucleic acid encoding a desired polypeptide), and a promoter. Additional factors necessary or helpful in effecting expression may also be used as described herein. For example, an expression cassette can also include nucleotide sequences that encode a signal sequence that directs secretion of an expressed protein from the host cell. Transcription termination signals, enhancers, and other nucleic acid sequences that influence gene expression, can also be included in an expression cassette. In preferred embodiments, a recombinant expression cassette encoding an amino acid sequence comprising a phage receptor is expressed in a bacterial host cell. In another embodiment, a recombinant expression cassette encoding an amino acid sequence comprising a therapeutic protein is expressed in a bacterial host cell. In a further embodiment, a polycistronic expression cassette encoding an amino acid sequence comprising a phage receptor is expressed in a bacterial host cell. In a further embodiment, a polycistronic expression cassette is expressed in a bacterial cell for production of more than one protein, e.g., a phage receptor and a therapeutic protein. In another example of expression of more than recombinant protein, an expression cassette can include more than one monocistronic expression cassette.

A "heterologous sequence" or a "heterologous nucleic acid", as used herein, is one that originates from a source foreign to the particular host cell, or, if from the same source, is modified from its original form. Thus, a heterologous phage receptor gene in a bacterial host cell includes a modified receptor-encoding gene that is endogenous to the particular host cell. Modification of the heterologous sequence may further occur, e.g., by treating the DNA with a restriction enzyme to generate a DNA fragment that is capable of being operably linked to the promoter. Techniques such as site-directed mutagenesis are also useful for modifying a heterologous sequence.

The term "operably linked" refers to functional linkage between a nucleic acid expression control sequence (such as a promoter, signal sequence, or array of transcription factor binding sites) and a second nucleic acid sequence, wherein the expression control sequence affects transcription and/or translation of the nucleic acid corresponding to the second sequence.

"Protein", "polypeptide", or "peptide" refer to a polymer in which the monomers are amino acids and are joined together through amide bonds, alternatively referred to as a polypeptide. When the amino acids are α-amino acids, either the L-optical isomer or the D-optical isomer can be used. Additionally, unnatural amino acids, for example, β-alanine, phenylglycine and homoarginine are also included. Amino acids that are not gene-encoded may also be used in the present invention. Furthermore, amino acids that have been modified to include reactive groups may also be used in the invention. All of the amino acids used in the present invention may be either the D- or L-isomer. The L-isomers are generally preferred. In addition, other peptidomimetics are also useful in the present invention. For a general review, see, Spatola, A. F., in CHEMISTRY AND BIOCHEMISTRY OF AMINO ACIDS, PEPTIDES AND PROTEINS, B. Weinstein, eds., Marcel Dekker, New York, p. 267 (1983).

The term "recombinant" when used with reference to a cell indicates that the cell replicates a heterologous nucleic acid, or expresses a peptide or protein encoded by a heterologous nucleic acid. Recombinant cells can contain genes that are not found within the native (non-recombinant) form of the cell. Recombinant cells can also contain genes found in the native form of the cell wherein the genes are modified and re-introduced into the cell by artificial means. The term also encompasses cells that contain a nucleic acid endogenous to the cell that has been modified without removing the nucleic acid from the cell; such modifications include those obtained by gene replacement, site-specific mutation, and related techniques. A "recombinant protein" is one which has been produced by a recombinant cell. In preferred embodiments, a recombinant phage receptor is produced by a recombinant bacterial cell.

III. General Antibiotic Resistance Mechanisms, MDR Clusters, Virulence Factors

As indicated above, antibiotics have revolutionized the practice of medicine for avoiding many of the problems presented by infectious diseases. The discovery of penicillin initiated this approach, and many different mechanisms of action to prevent growth of microbial flora have been exploited. In response, many bacterial mechanisms have evolved to evade the activities of antibiotics, and virtually all antibiotics have led to resistance strategies adopted by host targets. Among the many mechanisms of action, antibiotics have been developed which disrupt cell wall synthesis, cell membrane function, protein synthesis, nucleic acid synthesis, and metabolic action. Moreover, the many resistance means are often genetically clustered or linked together, often extrachromosomally, to be transferable between hosts in an efficient manner Generally, the extrachromosomal clusters are on R plasmids, but may be on other related genetic forms, e.g., F plasmids or phages. See, e.g., Torres, et al. (2007) "Current concepts in antibiotic-resistant gram-negative bacteria" *Expert Rev. Anti Infect. Ther.* 5(5):833-43.

Virulence factors are structures which provide functions important in microbial pathogenicity. See, e.g., Finlay and Falkow (1997) "Common themes in microbial pathogenicity revisited" *Microb. Mol. Biol. Rev.* 16: 136-169. Various definitions of microbial pathogenicity exist, and the pathogens can be distinguished from their non-virulent counterparts by the presence of such virulence genes. Several groups have explored the quandry of what exactly constitutes a virulence factor. It has been suggested that proteins thought of as necessary for pathogenicity fall into three categories: (1) "true" virulence genes, (2) those that are associated with virulence such as expression regulators of "true" factors, and (3) virulence "life-style" genes that are required by the bacterium to enable colonization of the host. In essence, a virulence factor is any moiety produced by a pathogen that is essential for causing disease in a host. See, e.g., Wassenaar and Gaastra (2001) "Bacterial virulence: can we draw the line?" *FEMS Microbiol. Lett.* 9995: 1-7.

Bacterial virulence factors can be roughly divided into several groups, based on the mechanism of virulence and function. These generally include adherence and colonization factors, invasins, capsules and surface components, endotoxins, exotoxins, siderophores, and toxin transporters.

The first host barrier for many invading pathogens is usually a mucosal surface, such as the gut or respiratory tract. Since epithelial cell turnover is around 48 hours in these environments, the bacterium must attach and replicate sufficiently to avoid being swept away. Therefore, many have evolved motile or attachment elements like flagella and pili/fimbriae to cross the barrier and invade. Simple attachment is mediated through a receptor on the host cell surface, and an adhesin on the bacterial one. Some may be species or even strain specific, while others exhibit tissue tropism, i.e., *Streptococcus mutans* will colonize teeth, but not the tongue epithelium. Other examples include the fimbrial protein subunit of *Vibrio, Neisseria*, and *Pseudomonas* spp. that bind D-Mannose on host cell surfaces. *Escherichia coli* also utilize this strategy, but can vary the fimbrial tip protein to bind other receptors like sialic acid (S-fimbriae).

Invasins differ from adherence factors by the fact they act extracellularly, breaking down host defenses at the local level and easing the passage of the infection. Most are enzymes, affecting physical barriers like tissue matrices and cell membranes. In this way, the bacterium can quickly spread through intercellular spaces. Some exotoxins may also have short lived invasion properties, but are distinguishable from true invasions, i.e., the pertussis toxin from *Bordetella*. There are several classes of invasive enzymes. Some dissolve hardy tissues like the hyaluronic component of connective tissue (*Clostridial hyaluronidase*). Other proteins punch holes in cell membranes and cause cell lysis (lecithinases and phospholipases from *Clostridium* and Gram positive cocci). Other obligate intracellular bacterial proteins (e.g., from *Listeria*) have been called "invasins" but these act exclusively on host actin filaments and induce engulfment of the microbe for colonization.

Capsules and surface components may be used to avoid phagocytosis. Many pathogens have evolved surface components that prevent the attachment and engulfment by macrophages and other host cellular immune responses. This may take the form of membrane bound proteins, slimy polysaccharide capsules, or "self" moieties scavenged by the microbe and bound to its cell surface. An example of the latter is *Treponema pallidum*, the causative agent of syphilis. The bacterium scavenges host fibronectin, and binds the moiety to its outer cell membrane.

Gram positive bacteria are naturally surrounded by a thick cell wall that has a low permeability to the surrounding environment, while Gram negative bacterial lipopolysaccharide (LPS) or "endotoxin" can protect against complement-mediated lysis. In addition, several antigens produced by both classes can inhibit adsorption, like Streptococcal Protein M, Staphylococcal Protein A, and the Vi antigen of *Salmonella typhi*.

Some pyogenic intracellular cocci also have the capacity to kill phagocytes. *Streptococcus pyogenes* and pathogenic Staphlyococci both excrete lytic enzymes, which cause neutrophil lysosomes to explode into the cytoplasm and kill host cells. The Gram negative *Pseudomonas aeruginosa* Exotoxin A can also kill phagocytes by halting the intracellular protein synthesis machinery.

Endotoxins are possessed almost solely by Gram negative organisms. Endotoxin or lipopolysaccharide (LPS) activates the host complement pathway, and is a potent inducer of inflammation. It is an outer membrane chemical moiety consisting of three sections: a toxic lipid (Lipid A) anchored in the outer membrane, an immunogenic polysaccharide core, and an antigenic O-linked series of oligosaccharides at the extracellular surface. It is considered a part of Gram negative bacterial pathology. Species as diverse as *Salmonella typhimurium* and *Neisseria meningitidis* express LPS on the cell surfaces.

Endotoxins are toxic to most mammals, and can be lethal if encountered in too high a dose. Specifically, release of LPS into the host circulation promotes binding by a certain protein, dubbed "LPS-binding complex". This interacts with CD14 receptors on a variety of monocytes and macrophages, triggering inflammatory cytokine release, and activation of the complement and coagulation cascades. Physiological distress involving pyrogenicity and mitogenicity eventually leads to blood sepsis and death. However, low levels of LPS used, e.g., as an adjuvant favorably increases the host's microbial resistance, and induces T-cells to produce more antiviral-enhancing γ interferon. The Lipid A component of LPS is a strong biological enhancer, and can boost the immune system.

Exotoxins are secreted by viable pathogenic cells. Bacterial protein exotoxins are amongst the most potent toxins known. Often encoded for by bacteriophage or plasmid, there are many classes, and all are strongly antigenic but inherently unstable. Some act on host cell surfaces, while the majority (A/B toxins) bind to the target membrane with a receptor (B subunit) and deliver a second moiety (A subunit) directly in to the cytoplasm. More specialized toxins involve "injection" of the protein into the host via a unique "type III" secretion system. The latter is only found in some Gram negative enteropathogens. Toxins can also be grouped according to their biological activity in certain cells, such as leukotoxins, neurotoxins, etc.

A well-studied, typical A/B toxin is diphtheria exotoxin (DT) from *Corynebacterium diptheriae*. The specific receptor used is heparin-binding epidermal growth factor; the A-subunit halts host protein synthesis and causes cell death. However, the toxin can also use host receptor-mediated endocytosis (RME) to enter the cell through an endosome. One A-subunit in the cytoplasm is enough to kill, and the bacterium can release up to 5,000 molecules an hour.

Surface acting toxins usually elicit their effects by binding to target cell molecules, or forming membrane pores through which cell lysis occurs. This group includes the vacuolating toxin of *Helicobacter pylori*, *E. coli* hemolysin, and "superantigens" belonging to *Streptococcus pyogenes* and *Staphylococcus aureus*. From elucidation of the crystal structure, one can clarify the function of such proteins at the molecular level. By non-specifically binding naïve T-cell receptors via MHC-II complexes, a massive inflammatory cytokine release is triggered, causing pyogenic fever like toxic shock syndrome.

The type III secretion systems of some Gram-negative enteropathogens are an unusual group of exotoxins. They are composed of two groups of proteins; structural moieties and effectors, that are encoded together on large pathogenicity islands on the bacterial chromosome. Although most TTSS protein structural components show sequence homology, the effectors affect the host cell in various ways in order to facilitate bacterial spread. For example, the six secreted Yop exotoxins of *Yersinia pestis* drastically affect the actin cytoskeleton, interfering with integrin-mediated phagocytosis and allowing uptake of the facultative intracellular bacterium. The Ipa proteins from *S. flexneri* contribute to the killing of neutrophils by necrosis, thus allowing the pathogen to enter host cells via disruption of the epithelial barrier. Some characteristics that these effectors share include: a lack of the traditional sec signal as seen in some other secreted exotoxins, extensive chaperoning by accessory proteins (also encoded in TTSS pathogenicity islands) while in the bacterial cytoplasm, and a possible translocation signal within the mRNA encoding each toxin.

The host environment is typically ideal for bacteria in every way except for one; iron is plentiful, but tightly bound in haem, ferritin, transferrin, or lactoferrin. It can be the limiting factor in infections. Therefore, some pathogens have evolved siderophore virulence factors that mediate the release of host iron for parasitic consumption. Examples include enterochelin from *Escherichia* and *Salmonella* spp, which scavenges bound iron from the host via high binding constants. Experiments involving a deletion of the seven enterochelin genes from *Salmonella* have shown that the pathogens lose their virulence when injected into mouse models. Thus, siderophores are essential for virulence.

Most Gram negative bacterial pathogens use four secretion systems to transport protein toxins from their cytoplasm into the host or extracellular matrix. Numbered Type I-IV respectively, the systems are used for different groups of exotoxins, such as the type 1 secretion of *E. coli* haemolysin through the periplasm. Although type 1 proteins possess a secretion signal, nothing is cleaved upon transport, and the whole process operates on a one-step mechanism involving a pore through inner and outer membranes. Many of the specifically secreted exotoxin genes are clustered on pathogenicity islands next to their respective secretion apparatus genes.

The majority of A/B exotoxins, like those of *Corynebacterium diphtheriae* and *Vibrio cholerae*, are transported to the bacterial cell surface via the two-step type II system. After cleavage of the amino terminus in the bacterial cytoplasm and transport of the protein through the sec machinery, a periplasmic intermediate is formed. This then passes through a second set of transmembrane proteins. Type IV secreted exotoxins also use the inner membrane sec proteins, but are passed through the outer membrane via their carboxyl terminus, like the CagA moiety of *Helicobacter pylori*. The type III secretion system, already described above, secretes effectors through a specialized macromolecular "needle" that injects exotoxins directly into the host cell cytoplasm.

These many virulence factors are often encoded on plasmids, which are transferred between host bacterial strains. The means to decrease the number of hosts or plasmids in a population which possess such plasmids may be achieved using the methods described herein. Plasmid or mobilizable element targets may be much broader than just antibacterial resistance plasmids, but include those which encode some or all of these various different virulence features.

IV. Conjugation Systems; Mobilizable Elements; DNA Transfer

A plasmid is typically a replicon, or replicating piece of DNA, that is stably inherited in an extrachromosomal state. In older literature, the term episome was used for plasmids capable of integration into the chromosome, but this term has largely gone into disuse. A plasmid typically exists as a covalently closed circular piece of double stranded DNA that has the capability of replicating autonomously and it is this property that leads to its isolation and physical recognition. The closed covalent nature of their structure allows them to be separated from chromosomal DNA by either gel electrophoresis or cesium chloride buoyant density gradients. See, e.g., bact.wisc.edu or basic textbooks or monographs on microbiology or molecular biology.

Two features are held in common by virtually all plasmids, they possess replication functions and typically fall into incompatability groups, which restrict which plasmids can coexist in a single host.

In the simplest case, the replication function derives from one or more origins of replication with the trans-acting proteins necessary for replication either being encoded by the plasmid itself or "borrowed" from the normal host replication machinery. The broad host range of some plasmids is at least in part explained by their multiple replication systems that allow them to function in a variety of dissimilar hosts, e.g., promiscuous replication origins, multiple alternative origins, a combination, or the like.

Plasmids typically fall into only one of the many existing incompatibility groups. Two plasmids are incompatible if either is less stable in the presence of the other than it was by itself. There are more than 30 incompatibility groups thus far described with no upper limit in sight. Incompatibility, whose genotypic designation is inc, is often a necessary consequence of a plasmid's desire to maintain a certain copy number in the cell. If plasmids of a given incompatibility group have a certain copy number that they attempt to maintain, then a competition will result when two plasmids of the same incompatibility group are found in the same cell. Whichever plasmid is able to replicate faster, or has some other advantage, will be represented to a disproportionate degree among the copies allowed by the incompatibility system. Surprisingly, plasmids can also be incompatible when they both possess the same functions for partitioning themselves into daughter cells.

A variety of additional features are often found in plasmids. Many plasmids contain genes uninvolved in either replication or incompatibility. Such genes can encode properties like antibiotic resistance (and therefore give rise to the terms "resistance" or "R" factors), degradation of complex macromolecules, production of bacteriocins, resistance to various heavy metals, synthesis of antibiotics, or virulence factors necessary for infection of animal or plant hosts A second common property is the ability to promote the transfer of the plasmid itself from one cell to another, termed conjugative ability. Conjugation is a unidirectional transfer of genetic information between cells by cell-to-cell contact. As such, it is not restricted to plasmids, but can occur with any DNA so long as the critical elements are present in the cell. This requirement for cellular contact distinguishes conjugation from transduction and transformation. The term "unidirectional" refers to the fact that a copy of the plasmid is transferred from one cell, termed the "donor", to another cell, termed the "recipient". There are two dissimilar functions involved in conjugative ability: the first is a site of initiation of transfer that is called either oriT or mob. The former term is a mnemonic for "origin of transfer" and the second is short for "mobility". In each case they refer to a site on the DNA and not to a diffusible product. A second group of functions are provided by proteins that act at these sites and cause the range of functions necessary for mobilization to occur. These are encoded by the tra genes and have a variety of functions including the formation of the pilus that makes contact with the recipient cell and seems to be involved in drawing the donor and recipient cells together. This brings about a region of membrane contact and it appears a conjugation bridge of some sort is formed. The products of the tra genes are involved in both the regulation and the physical construction of these events. Some event in this sequence triggers the nicking of a site, termed oriT, by a specific single-strand nuclease and a subsequent binding of one or more "pilot" proteins to the free 5' end of the DNA. These proteins seem to function in the subsequent replication of the transferred DNA with one serving as a "primase". A single-strand is then transferred from this end to the recipient while a "rolling circle" form of replication occurs in the donor. If the DNA being transferred is a plasmid, it is made double-stranded and circularized in the recipient, whereupon it can presumably replicate. If the transfer DNA is chromosomal, circularization cannot occur, but in some way a complementary strand is generated and homologous recombination with the chromosome can occur (in any case, the incoming DNA becomes associated with a replicon if it is to be inherited). It is possible for a plasmid to be non-conjugative and yet mobilizable (if the tra products are supplied by another plasmid) so long as an oriT site is encoded on the plasmid (whoever has the oriT site is transferred). Finally, a plasmid lacking both the tra functions and oriT functions would be non-conjugative and non-mobilizable. Many applications in inverse genetics employ small plasmids containing oriT regions, where the tra functions are supplied by another plasmid in the cell.

Plasmids often have mechanisms that increase the likelihood that, following cell division, both daughter cells will contain a copy of the plasmid. The partition functions (often termed par) responsible for this work by a variety of mechanisms including monomerization of plasmid multimers (better to have many monomers than a few multimers) and association of the plasmid with membranes (which apparently helps physically separate the plasmids). While we refer to a plasmid being "lost" by a cell, the actual mechanism is almost certainly that the cell never received the plasmid at the previous cell division due to inappropriate partitioning. Such loss is termed segregation. For both low and high copy-number plasmids, this "loss" occurs at (very roughly) 1% frequency, though some exceptionally stable plasmids have been found, presumably because of a set of different par functions. Some plasmids have evolved a system, with effects like the par systems, that "prevents" segregation by killing any daughter cell that has not received a plasmid. They do this by producing a relatively long-lived killing function (kil) and a short-lived kill override (kor) function. A daughter without the plasmid will have the kil product, but will not be able to maintain the necessary amount of kor product to survive. To the experimenter, these systems will look like partitioning systems, since, in mutants lacking these, plasmid-free segregants will be more frequently detected. They can also appear to be inc functions.

Occasionally, it is necessary to isolate a plasmid-free derivative of a strain currently containing a plasmid, a procedure termed curing. These can be sought (i) spontaneously (perhaps replica printing isolated colonies if the plasmid confers a scorable phenotype); (ii) following an enrichment (again, if the plasmid confers a growth phenotype); (iii) by selecting a different, but incompatible, plasmid into the cell; or (iv) by treatment with elevated temperature or chemicals such as acridines, ethidium bromide, sodium dodecyl sulfate and novobiocin (since the first two chemicals are known as mutagens, they should be used with restraint). In particular, the invention provides a form of "curing" by eliminating those cells which possess the plasmid conferring phage binding or infection sensitivity.

F factor is the best studied of the incompatibility groups that have the property of conjugative ability. In its extrachromosomal state the factor has a molecular weight of approximately 62 kb and encodes at least 20 tra genes. It also contains three copies of IS3, one copy of IS2, and one copy of a Å sequence as well as genes for incompatibility and replication. The F factor can exist in three different states: "F+" refers to a factor in an autonomous, extrachromosomal state containing only the genetic information described above. The "Hfr" (which refers to "high frequency recombination") state describes the situation when the factor has integrated itself into the chromosome presumably due to its various insertion sequences. Finally, the "F'" or (F prime) state refers to the factor when it exists as an extrachromosomal element, but with the additional requirement that it contain some section of chromosomal DNA covalently attached to it. A strain containing no F factor is said to be "F−".

In mating an F+ with an F− strain, one finds fast, efficient transfer of F+ (approximately 50% transfer in one hour), but chromosomal transfer is only at the level of 10E-5 to 10E-7 per donor cell. This is probably due to rare, spontaneous Hfr formation. As mentioned above, Hfr's arise by integration into the chromosome due to the insertion sequences on the plasmid. These seem to cause integration at preferred sites, so that one finds a variety of different Hfr's which differ with respect to their origins of transfer and direction of transfer. When one performs a cross between an Hfr strain and an F− strain, one sees transfer of chromosomal markers at high frequency (10E-2 to 10E-5). This transfer is both oriented and time dependent. Since transfer begins at the oriT site in the F factor, a portion of the F factor is transferred first followed by the remainder of the chromosome. If the entire chromosome is transferred, then the other portion of the F factor is transferred. The F factor itself does not integrate into the recipient as there is no homology for such integration but the chromosomal DNA which has been transferred can recombine in by homologous recombination. The transfer of the entire E. coli chromosome takes approximately 100 minutes but you very often get spontaneous breakage of the mating pair. Such breakage means that markers transferred late are often not transferred at all yielding a gradient of transfer which tends to be of the order of 10E3 (that is, early markers are transferred approximately 10E3 times more frequently than the most distal markers). The net result is that one often fails to transfer the entire chromosome. In crosses between an F' and an F− strain, two possible donation events can occur, depending on the genotype of the donor. If the donor strain is Rec−, then the plasmid will remain as an extrachromosomal element in the donor and will be the only genetic information transferred in the conjugation event. If, however, the donor cell is Rec+, then homologous recombination will cause some of the F's to integrate into the chromosome of the donor and thus act like Hfr's. Typically, for that reason, Rec− donors are used for such analyses.

A "limitation" of classic F factors is that their use is generally restricted to E. coli and its close relatives. In these organisms, F's are large, low-copy, conjugative plasmids capable of chromosomal mobilization, but are too large to physically handle with any ease. New variants, e.g., engineered versions, will be created for use in methods described, or optimized for efficiency of transfer, expression, or susceptibility by targeting phage. Some preferred new variants are smaller, e.g., comprise fewer nucleotides, than the naturally occurring F factors. Other new variants of classical F factors provide closer linkage between, e.g., an origin of replication and a nucleic acid that encodes a tectivirus receptor.

Plasmids of a variety of other incompatibility groups, with a wide range of properties, have been useful in genetic analysis. Natural isolates vary in copy number (from approximately one per cell to hundreds), size (several kB to hundreds of kB), stability, conjugative ability, host range, and drug resistance. Moreover, because many of these properties are the product of one or a small set of genes, a vast array of plasmids have been engineered to have a specific set of useful properties, including a number of unique cloning sites for in vitro manipulation. Specialized manuals describe the general choices and new versions are constantly being described in the literature.

The term "mating pair formation system" is applicable to plasmids for conjugation, along with other systems which allow for the effective transfer of DNA, e.g., by transduction or transformation. See, e.g., Schrodera and Lankab (2005) "The mating pair formation system of conjugative plasmids—A versatile secretion machinery for transfer of proteins and DNA" *Plasmid* 54:1-25; Dale and Park (2004) *Molecular Genetics of Bacteria* (4th ed.) Wiley ISBN-10: 047085085X, ISBN-13: 978-0470850855; Brooks (2007) *Medical Microbiology* (24th ed.) McGraw-Hill Medical, ISBN-10: 0071476660, ISBN-13: 978-0071476669; Demuch and Lamont (eds. 2006) *Bacterial Cell-to-Cell Communication: Role in Virulence and Pathogenesis* (Advances in Molecular and Cellular Microbiology) Cambridge University Press, ISBN-10: 0521846382, ISBN-13: 978-0521846387; Phillips (ed. 2004) *Plasmid Biology* ASM Press; ISBN-10: 1555812651, ISBN-13: 978-1555812652; Thomas (2000) *Horizontal Gene Pool: Bacterial Plasmids and Gene Spread* CRC Press, ISBN-10: 9057024624, ISBN-13: 978-9057024627; and other microbiology or bacteriology textbooks.

In the context of a conjugation mechanism, cells can be converted from F− to F+ in the population. As the plasmids also often carry the resistance markers, selection in the context of an antibiotic will ensure that the plasmid containing phenotype becomes predominant. Where the plasmid also encodes the receptor for a phage, the linkage of the resistance marker with the phage susceptibility marker provides for the combination of antibiotic plus phage exposure to significantly decrease the bacterial population, sufficient for the immune or other host bacterial elimination systems to minimize the population. In many cases, the combination may function synergistically, such that subthreshold amounts of the antibiotic and phage may effectively control the infection. In addition, the temporal treatments with the phage and antibiotic may be overlapping or separate.

V. Broad Host Range Phage; Tectiviridae Genus

Classical phage dogma states that phage binding and infection are extremely narrow host range processes, and that most phage lack the capacity to bind and/or replicate in a multiplicity of different hosts. The description of the Tectiviridae family of phages suggests that the peculiar nature of broad host range is unusual. The specific mechanisms of narrow host range may be due to selective observation, and a combination of typically highly specialized interaction of both host cell binding, infection, replication, and lysis functions.

In contrast, recognizing the potential value of broad host range phage, means selection for trait of broad selectivity can be performed. Starting with a phage having relatively broad host range, selection methods to broaden its host specificity can be applied. Mutagenesis of the phage host specificity components, e.g., the specificity binding proteins at the ends of tail fibers, can be performed. Binding specificity conferring genes can be identified by standard genetic means to identify what phage proteins are involved. For example, in the PRD1 phage, the P2 protein has been identified as the major target cell receptor. Combined studies on both the phage receptor and the host protein will be able to broaden the range of binding, and bioinformatic analysis can also identify other species which express similar phage receptors. Structural analysis of the receptor-binding protein interaction will allow for mutagenesis or design of target receptors which will be recognized by less selective binding proteins.

Besides binding specificity, some of the host range restriction may have to do with the later steps in phage infection after binding. Thus, infection, replication, and lysis functions will be modified to broaden promiscuity to successfully occur in a broader range of host strains. Alternatively, restrictive regulation of these functions may be relaxed by mutagenesis and selection processes.

In particular, it will be desirable to find means to span restrictive function across the Gram-negative and Gram-positive divide, which reflects structural differences between the outer cell wall structures. In particular, the cell wall structure of Gram-positive bacteria is seemingly similar to the inner cell wall structure of the Gram-negative bacteria. As such, common structural features of hosts within Gram-negative bacteria will be susceptible to phage which can reach those structures. Thus, it may be useful to combine or modify the phages to incorporate means to digest the local regions of the outer cell wall of the Gram-negative strains. The enzymatic activities to do so would be present on normal phage which attack Gram-negative bacteria from outside the outer cell wall. See Padmanabhan, et al. "Phage Derived Antimicrobial Activities" WO/2007/130655. Whether the enzymatic activity is attached to the phage or separately administered, the digestion of the outer cell wall may provide accessibility for the phage to contact the inner cell membrane.

It should be noted that in certain circumstances, the host cell may become incapacitated in spite of an abortive infection. The infection process may fail for failure of replication or lytic functions, while the infection process of injection of the DNA may itself incapacitate and kill the cell without producing more phage. In certain circumstances, this achieves the intended result of preventing the host bacteria cell from further growth or virulence functions, or serving as a reservoir for a plasmid which conferred phage sensitivity and/or antibiotic resistance to the bacterial cell.

Non-tectiviridae broad host range viruses would also be useful in this similar fashion. Other phages whose receptors can be associated with plasmids encoding virulence or resistance factors will be useable. It will be particularly useful to generate plasmids which link the relevant selection markers, whether antibiotic resistance or virulence, to components of the receptor for an appropriate bacteriophage. See, e.g., Gaidelyte, et al. (2006) *J. Bact.* 188:5925-5934.

In other related embodiments, promiscuous (e.g., broader phage spectrum) or multiple closely related receptors may be designed or generated to which related phage from different sources can bind. A "universal" phage may be constructed which may bind to many different host bacteria. An infective mechanism applicable to many different bacterial hosts may be combined with the initial binding or recognition function provided.

In an alternative embodiment, where the mobilizable element transfer a different marker which can be used to mark recipient target cells, the marker may be, e.g., a receptor for a target moiety or a recognition element for killing the expressing cell. For example, the receptor may be a high affinity receptor for a toxic entity such as a toxic conjugate or may be a receptor for another killing system, e.g., macrophage phagocytosis or immune component.

VI. Artificial Mobilizable Element Constructs; Plasmids with Receptor Genes

The methods of the present invention may be accomplished more effectively, in many cases, by generating artificial constructs instead of using natural isolates to achieve the results. For example, particular versions may be constructed which improve on natural isolates of plasmids or phage. Modifications may be incorporated into resistance or virulence markers. Variant engineered forms from the markers naturally evolved, e.g., to counter therapeutically useful antibiotics, might be used to provide an increased selectivity for resistance to an alternative related selective means. A different antibiotic, e.g., a related compound, might be used to select plasmids encoding the variant marker, which might be more closely linked to one or more desired receptors for expression. The population of bacteria may be subjected to the alternative selective marker to more strongly select for the desired version of mobilizable element which provides better efficiency of host destruction with the broad spectrum phage. Alternatively, the variant marker may be linked to a higher expression level receptor or to a receptor exhibiting higher affinity or efficiency in host killing by the corresponding phage. Phage might be constructed which have better efficiency or features in killing hosts expressing the defined receptors.

In other embodiments, the mobilizable element may be engineered to have advantageous features for the methods described. The plasmids may be designed to exhibit, e.g., higher efficiency transfer to new hosts, better expression within hosts, improved receptor properties, changed efficiency in DNA methylation leading to changed expression levels of encoded nucleic acids, removal of extraneous plasmid size or structure, additional trackable features, and the like. The phage or mobilizable elements may be designed to function more efficiently under the conditions of use, e.g., under chemical or physical conditions of use. Formulations of the materials may also be designed to the specific environment of use, whether topical, surface, mucosal, solution, etc.

The means to design or identify broader spectrum receptors recognized by different phages exist. Thus, receptors may be screened or selected across many different tectivirus phage or the like. Selected or natural variants may be screened and identified. Modified affinity or selectivity will be important under appropriate uses. In other situations, means may be applied to change the features of a given receptor, e.g., changing the physical environment by salt, pH, polarity, and such may cause conformational changes which affect function of the ligand-receptor interactions. See description of plasmid dependent phages and corresponding plasmids, above.

In certain situations, it may be useful to identify systems which function at environmental extremes relative to the normal laboratory conditions. Selection for systems which function at low or high temperatures, e.g., efficient pilus expression allowing for more efficient transfer to broad population under extremes of environmental conditions relative to laboratory conditions. Ambient room or environmental temperatures may be where the methods are applied for environmental remediation.

In addition, the phage functions desired may often be achieved using less than intact phage. Phage fragments or parts, e.g., pyocins, tails, enzymes, etc. may substitute for intact tectivirus in effectively compromising genetic functions. The functions of mobilizable elements may be compromised with indirect degradation of the nucleic acids which occur when cells are disrupted.

VII. Practical Applications

Practical applications of the present invention include, e.g., public health water and waste treatment, treating of bacteria in hospital settings, food processing, therapeutic or environmental elimination of resistance or virulence encoding plasmids, effective sensitization or evaluation/detection of infection, and selective pressure to acquire plasmid followed by a step to kill plasmid containing cells. Other applications include reduction of bacterial species with plasmids can be performed on animal facilities, e.g., on appropriate surfaces of the buildings and equipment where presence of harmful bacteria is undesirable. In addition, the methods can be applied to farm animals, e.g., (dairy and beef cattle, pigs, chicken, fish, shrimp, and the like) application to reduce over all presence of bacteria containing undesirable plasmid elements.

One important application is treatment of articles which may be contaminated in normal use, e.g., catheters, hospital monitor systems, clinical instruments, and equipment. Locations, equipment, environments, or the like where target bacteria may be public health hazards may be treated using the methods and compositions provided. Locations of interest include public, particularly public health, facilities where the purpose or opportunity exists to deal with target bacteria containing materials, especially those with the virulence or antibiotic resistance markers. These materials may include waste products, e.g., liquid, solid, or air. Surfaces which are touched by many people are important, including door handles, faucets, elevator buttons, etc.

Aqueous waste treatment plants may incorporate these methods to eliminate the target host or mobilizable element from effluent. Solid waste sites may introduce these methods to minimize possibility of outbreaks of infections or release of the mobilizable elements which could transmit their genes to the wrong places. Conversely, food preparation areas or equipment need to be regularly cleaned, and the invention provides compositions and means to effectively eliminate target bacteria, especially the most dangerous ones harboring the mobilizable elements. Medical and other public environments subject to contamination may warrant similar means to minimize growth and spread of target microorganisms and transfer of selected mobilizable elements. The methods may be used in contexts where sterilization elimination of target bacteria is desired, including air filtration systems, e.g., for an intensive care unit or limited circulation environment as airplanes, submarines, etc.

Alternative applications include use in a veterinary or medical context. Means to determine the presence of particular bacteria, or to identify specific targets may identify additional sources for use of these techniques. Inclusion of bacteriocidal or bacteriostatic activities to cleaning agents, including washing of animals and pets, may be applied in combination with these techniques.

The phage can be used to eliminate hosts which possess the plasmids which confer susceptibility. Under antibiotic selective conditions requiring hosts to possess the resistance gene containing plasmid, the hosts also would express the phage receptor making those cells sensitive to phage infection, and thereby killing cells containing the plasmid.

The methods of the invention can be used to transfer phage susceptibility between bacterial species that would not typically interact. As an example, conjugative plasmids that are transferred between bacteria that typically have animal, e.g., vertebrate or mammalian, hosts, can be transferred to bacterial that typically infect different hosts, e.g., invertebrates, such as insects, or plants. Alternatively, the bacteria that typically infect plant or invertebrate hosts can be sued as a source of a conjugative plasmid for transfer to bacteria that typically have a vertebrate or mammalian host. Exemplary species amenable for this transfer are, e.g.,

*Salmonella* bacteria and *Xanthomonas* bacteria. In one embodiment, a conjugative plasmid encoding a receptor for the tectivirus PRD1 phage, is transferred from an *S. typhimurium* bacterial cell to an *X. campestris* bacterial cell. The transfer of the conjugative plasmid renders the *X. campestris* host cell susceptible to infection by the tectivirus, and, therefore, to killing or reduction in cell replication rate. Example 8, herein, provides a demonstration of the transfer of a conjugative plasmid from a *Salmonella* bacteria to a *Xanthomonas* bacteria.

The methodology may also be used to eliminate plasmids in the population which carry the antibiotic resistance markers. Thus, in certain contexts, the methods may be used to reduce the prevalence of resistance genes in a defined bacterial population or culture. These methods may be combined with other treatments, e.g., treatment with additional antimicrobial methods or compositions, or may be combined with compounds which induce F pili formation. See, e.g., Hergenrother, et al. "Methods of Treating Drug-Resistant Bacterial Infections" US Patent publication 20030130169, U.S. Ser. No. 10/261,851, and related compositions. The combinations may be administered together or in succession.

The plasmids may also be used to confer sensitivity to phage infection by transferring the genes encoding receptors onto cells which otherwise lack the receptor. In this way, means are provided to convert phage nonsusceptible hosts into susceptible hosts.

VIII. Therapeutic Administration

The methods applied or route of administration and dosage will vary with the infecting bacteria strain(s), the site and extent of infection (e.g., local or systemic), the marker or receptor being used, and the subject being treated. The routes of administration, whether for the plasmid or phage, include but are not limited to: oral, aerosol or other device for delivery to the lungs, nasal spray, intravenous (IV), intramuscular, intraperitoneal, intrathecal, intraocular, vaginal, rectal, topical, lumbar puncture, intrathecal, and direct application to the brain and/or meninges. Excipients which can be used as a vehicle for the delivery of the therapeutic will be apparent to those skilled in the art. For example, the plasmid or phage could be in lyophilized form and be dissolved just prior to administration by IV injection. The dosage of administration is contemplated to be in the range of about 0.03, 0.1, 0.3, 1, 3, 10, 30, 100, 300, 1000, 3000, 10000 or more plasmid molecules per bacterium in the host infection. Depending upon the size of the plasmid, which may itself be tandemly associated, or in multiple copy form (dimer, trimer, tetramer, pentamer, and the like) or in combination with one or more other entities, e.g., fragments or different adjuvants, the dose may be about 1 million to about 10 trillion/per kg/per day, and preferably about 1 trillion/per kg/per day. In the later steps of phage administration, the doses may be in the range of about 0.03, 0.1, 0.3, 1, 3, 10, 30, 100, 300, 1000, 3000, 10000 or more phage particles per bacterium in the host infection, or from about 10E6 bacteria killing units/kg/day to about 10E13 killing units/kg/day.

Methods to evaluate killing capacity may be similar to methods used by those of skill to evaluate intact replicating phage, e.g., plaque forming units or pfu, though killing units may be better evaluated by determining the number of surviving bacteria after titration of the killing units. Killing quantitation is more distinct, however, since non-replicating phage particles may not form plaques on bacterial host lawns. Thus, serial dilution methods to evaluate the quantity of "killing" units are conveniently used in place of standard pfu. Serial dilutions of bacterial cultures exposed to the killing compositions can quantitate killing units. Alternatively, comparing total bacterial counts with viable colony units can establish what fraction of bacteria is actually viable, and by implication, what fraction have been susceptible to the killing constructs. Other measures of activity on artificial or specially prepared substrates can often be used as surrogate measures of killing units.

The therapeutic(s) are typically administered or titrated until successful elimination of the pathogenic plasmid is achieved, though broad spectrum formulations may be used while specific diagnosis of the infecting strain is being determined Thus the invention contemplates single dosage forms, as well as multiple dosage forms of the compositions of the invention, as well as methods for accomplishing sustained release means for delivery of such single and multi-dosages forms. Delayed release formulations of killing phage may be combined with earlier or immediate plasmid transfer, e.g., administration of mobilizable element systems.

With respect to the aerosol administration to the lungs or other mucosal surfaces, the therapeutic composition is incorporated into an aerosol formulation specifically designed for administration. Many such aerosols are known in the art, and the present invention is not limited to particular formulations. An example of such an aerosol is the Proventil inhaler manufactured by Schering-Plough, the propellant of which contains trichloromonofluoro-methane, dichlorodifluoromethane, and oleic acid. Other embodiments include inhalers that are designed for administration to nasal and sinus passages of a subject or patient. The concentrations of the propellant ingredients and emulsifiers are adjusted if necessary based on the specific composition being used in the treatment. The number of phage killing units to be administered per aerosol treatment will typically be in the range of about 10E6 to 10E13 killing units, and preferably about 10E12 killing units.

Typically, the killing will decrease the host replication capacity by at least about 3 fold, and may affect it by about 10, 30, 100, 300, etc., to many orders of magnitude. However, even slowing the rate of host replication without killing may have significant therapeutic or commercial value. Preferred genetic inactivation efficiencies may be 4, 4.5, 5, 5.5, 6, 6.5, 7, 8, or more log units. Similarly, reduction in rates of increase or absolute plasmid prevalence or number increase per host bacteria cell may be useful measures, and will preferably result in decreases of at least about 3, 10, 30, 100, or 300 fold relative to non-treatment.

IX. Formulations

The invention further contemplates pharmaceutical compositions comprising a plasmid and/or phage of the invention provided in a pharmaceutically acceptable excipient. The formulations and pharmaceutical compositions of the invention thus contemplate formulations comprising an isolated plasmid segment capable of being transferred to the specific bacterial host; a mixture of two, three, five, ten, or twenty or more entities that affect the same or typical bacterial hosts; or a plasmid encoding two, three, five, ten, or twenty or more receptors that affect different bacterial hosts or different strains of the same bacterial host. There may instances in which it will be useful to use a cocktail mixture of plasmids that collectively inhibit the growth of multiple strains of bacteria, e.g., *Staphylococcus aureus*. In this manner, the compositions of the invention can be tailored to the needs of the intended use. The compounds or compositions will typically be sterile or near sterile.

By "therapeutically effective dose" herein is meant a dose that produces effects, e.g., bacteriostatic or preferably bactericidal, for which it is administered. In the context of plasmid elimination, it may be measured in a decreased rate of numbers or growth among bacterial population members. The exact dose will depend on the purpose of the treatment, and will be ascertainable by one skilled in the art using known techniques. See, e.g., Ansel, et al. *Pharmaceutical Dosage Forms and Drug Delivery*; Lieberman (1992) *Pharmaceutical Dosage Forms* (vols. 1-3), Dekker, ISBN 0824770846, 082476918X, 0824712692, 0824716981; Lloyd (1999) *The Art, Science and Technology of Pharmaceutical Compounding*; and Pickar (1999) *Dosage Calculations*. As is known in the art, adjustments for plasmid or phage degradation, systemic versus localized delivery, and rate of plasmid transfer, as well as the age, body weight, general health, sex, diet, time of administration, drug interaction, spectrum of bacterial components in the colony, and the severity of the condition may be necessary, and will be ascertainable with some experimentation by those skilled in the art.

Various pharmaceutically acceptable excipients are well known in the art. As used herein, "pharmaceutically acceptable excipient" includes a material which, when combined with an active ingredient of a composition, allows the ingredient to retain biological activity and without causing disruptive reactions with the subject's immune system. Such may include stabilizers, preservatives, salt, or sugar complexes or crystals, and the like.

Exemplary pharmaceutically carriers include sterile aqueous of non-aqueous solutions, suspensions, and emulsions. Examples include, but are not limited to, standard pharmaceutical excipients such as a phosphate buffered saline solution, water, emulsions such as oil/water emulsion, and various types of wetting agents. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. In other embodiments, the compositions will be incorporated into solid matrix, including slow release particles, glass beads, bandages, inserts on the eye, and topical forms.

A composition comprising a composition of the invention may also be lyophilized using means well known in the art, e.g., for subsequent reconstitution and use according to the invention.

Also of interest are formulations for liposomal delivery, and formulations comprising microencapsulated enzymes, including sugar crystals. Compositions comprising such excipients are formulated by well known conventional methods (see, e.g., Remington's *Pharmaceutical Sciences*, Chapter 43, 14th Ed., Mack Publishing Col, Easton Pa. 18042, USA). Delayed release formulations for phage may be applied after the plasmid mobilization step, which may allow a single combined administration step.

In general, pharmaceutical compositions can be prepared in various forms, such as granules, tablets, pills, suppositories, capsules (e.g. adapted for oral delivery), microbeads, microspheres, liposomes, suspensions, salves, lotions and the like. Pharmaceutical grade organic or inorganic carriers and/or diluents suitable for oral and topical use can be used to make up compositions comprising the therapeutically-active compounds. Diluents known to the art include aqueous media, vegetable and animal oils and fats. Formulations may incorporate stabilizing agents, wetting and emulsifying agents, salts for varying the osmotic pressure or buffers for securing an adequate pH value.

The pharmaceutical composition can comprise other components in addition to the active composition. In addition, the pharmaceutical compositions may comprise more than one active ingredient, e.g., two or more, three or more, five or more, or ten or more different entities, where the different plasmids or phage may be specific for the same, different, or accompanying bacteria. For example, the pharmaceutical composition can contain multiple (e.g., at least two or more) plasmids, wherein at least two of the plasmids in the composition have different bacterial host specificity for transfer. In this manner, the therapeutic composition can be adapted for treating a mixed infection of different bacteria, or may be a composition selected to be effective against various types of infections found commonly in a particular institutional environment. A select combination may result, e.g., by selecting different groups of plasmid entities so as to contain at least one component effective against different or critical bacteria (e.g., strain, species, etc.) suspected of being present in the infection (e.g., in the infected site). As noted above, the composition can be administered in conjunction with other agents, such as a conventional antimicrobial agent. In some embodiments, it may be desirable to administer the plasmid and phage within the same formulation, which may have different rates of release of the plasmid and phage components.

X. Methodology

Some aspects of practicing the present invention involve well-known methods general clinical microbiology, general methods for handling bacteriophage, and general fundamentals of biotechnology, principles and methods. References for such methods are listed below and are herein incorporated by reference for all purposes.

A. General Clinical Microbiology

General microbiology is the study of the microorganisms. See, e.g., Sonenshein, et al. (eds. 2002) *Bacillus Subtilis and Its Closest Relatives: From Genes to Cells* Amer. Soc. Microbiol., ISBN: 1555812058; Alexander and Strete (2001) *Microbiology: A Photographic Atlas for the Laboratory* Benjamin/Cummings, ISBN: 0805327320; Cann (2001) *Principles of Molecular Virology* (Book with CD-ROM; 3d ed.), ISBN: 0121585336; Garrity (ed. 2005) *Bergey's Manual of Systematic Bacteriology* (2 vol. 2d ed.) Plenum, ISBN: 0387950400; Salyers and Whitt (2001) *Bacterial Pathogenesis: A Molecular Approach* (2d ed.) Amer. Soc. Microbiol., ISBN: 155581171X; Tierno (2001) *The Secret Life of Germs: Observations and Lessons from a Microbe Hunter* Pocket Star, ISBN: 0743421876; Block (ed. 2000) *Disinfection, Sterilization, and Preservation* (5th ed.) Lippincott Williams & Wilkins Publ., ISBN: 0683307401; Cullimore (2000) *Practical Atlas for Bacterial Identification* Lewis Pub., ISBN: 1566703921; Madigan, et al. (2000) *Brock Biology of Microorganisms* (9th ed.) Prentice Hall, ASIN: 0130819220; Maier, et al. (eds. 2000) *Environmental Microbiology* Academic Pr., ISBN: 0124975704; Tortora, et al. (2000) *Microbiology: An Introduction* including Microbiology Place™ Website, Student Tutorial CD-ROM, and Bacteria ID CD-ROM (7th ed.), Benjamin/Cummings, ISBN 0805375546; Demain, et al. (eds. 1999) *Manual of Industrial Microbiology and Biotechnology* (2d ed.) Amer. Soc. Microbiol., ISBN: 1555811280; Flint, et al. (eds. 1999) *Principles of Virology: Molecular Biology, Pathogenesis, and Control* Amer. Soc. Microbiol., ISBN: 1555811272; Murray, et al. (ed. 1999) *Manual of Clinical Microbiology* (7th ed.) Amer. Soc. Microbiol., ISBN: 1555811264; Burlage, et al. (eds. 1998) *Techniques in Microbial Ecology* Oxford Univ. Pr., ISBN: 0195092236; Forbes, et al. (1998) *Bailey & Scott's Diagnostic Microbiology* (10th ed.) Mosby, ASIN: 0815125356; Schaechter, et al. (ed. 1998) *Mechanisms of Microbial Disease* (3d ed.) Lippincott, Williams & Wilkins, ISBN: 0683076051; Tomes (1998) *The Gospel of Germs: Men, Women, and the Microbe in American Life* Harvard Univ. Pr., ISBN: 0674357078; Snyder and Champness (1997) *Molecular Genetics of Bacteria* Amer. Soc. Microbiol., ISBN: 1555811027; Karlen (1996) *MAN AND MICROBES: Disease and Plagues in History and Modern Times Touchstone Books*, ISBN: 0684822709; and Bergey (ed. 1994) *Bergey's Manual of Determinative Bacteriology* (9th ed.) Lippincott, Williams & Wilkins, ISBN: 0683006037.

B. General Methods for Handling Bacteriophage

General methods for handling bacteriophage are well known, see, e.g., Snustad and Dean (2002) *Genetics Experiments with Bacterial Viruses* Freeman; O'Brien and Aitken (eds. 2002) *Antibody Phage Display: Methods and Protocols* Humana; Ring and Blair (eds. 2000) *Genetically Engineered Viruses* BIOS Sci. Pub.; Adolf (ed. 1995) *Methods in Molecular Genetics: Viral Gene Techniques* vol. 6, Elsevier; Adolf (ed. 1995) *Methods in Molecular Genetics: Viral Gene Techniques* vol. 7, Elsevier; and Hoban and Rott (eds. 1988) *Molec. Biol. of Bacterial Virus Systems* (Current Topics in Microbiology and Immunology No. 136) Springer-Verlag.

C. General Fundamentals of Biotechnology, Principles and Methods

General fundamentals of biotechnology, principles and methods are described, e.g., in Alberts, et al. (2002) *Molecular Biology of the Cell* (4th ed.) Garland ISBN: 0815332181; Lodish, et al. (1999) *Molecular Cell Biology* (4th ed.) Freeman, ISBN: 071673706X; Janeway, et al. (eds. 2001) *Immunobiology* (5th ed.) Garland, ISBN: 081533642X; Flint, et al. (eds. 1999) *Principles of Virology: Molecular Biology, Pathogenesis, and Control*, Am. Soc. Microbiol., ISBN: 1555811272; Nelson, et al. (2000) *Lehninger Principles of Biochemistry* (3d ed.) Worth, ISBN: 1572599316; Freshney (2000) *Culture of Animal Cells: A Manual of Basic Technique* (4th ed.) Wiley-Liss; ISBN: 0471348899; Arias and Stewart (2002) *Molecular Principles of Animal Development*, Oxford University Press, ISBN: 0198792840; Griffiths, et al. (2000) *An Introduction to Genetic Analysis* (7th ed.) Freeman, ISBN: 071673771X; Kierszenbaum (2001) *Histology and Cell Biology*, Mosby, ISBN: 0323016391; Weaver (2001) *Molecular Biology* (2d ed.) McGraw-Hill, ISBN: 0072345179; Barker (1998) *At the Bench: A Laboratory Navigator* CSH Laboratory, ISBN: 0879695234; Branden and Tooze (1999) *Introduction to Protein Structure* (2d ed.), Garland Publishing; ISBN: 0815323050; Sambrook and Russell (2001) *Molecular Cloning: A Laboratory Manual* (3 vol., 3d ed.), CSH Lab. Press, ISBN: 0879695773; and Scopes (1994) *Protein Purification: Principles and Practice* (3d ed.) Springer Verlag, ISBN: 0387940723.

D. Transcriptional Regulation of Protein Expression

Transcription is a process whereby a DNA sequence, for instance, from a vector, is copied by an RNA polymerase to produce a product RNA, e.g., a messenger RNA or mRNA. For protein or peptide expression, transcription of mRNA is potentially a regulated step and thus, ultimately affects the expression level of a recombinant protein or peptide.

Transcription is initiated by binding of RNA polymerase to a promoter region in the DNA sequence. A promoter is a positive regulatory region for DNA expression that is located upstream (in the 5' region) of the gene to be transcribed. Transcription can also be regulated in a negative manner by, e.g., binding of a repressor protein to repressor DNA sequences, typically located near promoter sequences.

To regulate transcription of recombinant proteins, an expression cassette can include multiple promoters and also negative regulatory sequence, e.g. repressor protein binding sites. The tac promoter, considered to be a strong promoter, is described by de Boer and colleagues (de Boer et al., *PNAS* 80:21-25 (1983). Generally speaking, the level of nucleic acid expression is believed to increase as promoters increase in both number and relative strength. Other promoters that can be used include the Tac promoter, Other exemplary promoters include, e.g., a T7 promoter, a T5 promoter, the $P_R$ promoter, the $P_L$ promoter, the trp promoter, the lac promoter, the araB promoter, and the gal promoter.

In some embodiments of the present invention, any number and combination of the lac and tac promoters are designed into the vector.

E. Mutagenesis; Site Specific, Random, Shuffling

Based upon the structural and functional descriptions provide herein, homologs and variants may be isolated or generated which may optimize preferred features. Thus, additional catalytic segments of plasmid transfer, receptor expression, phage binding, or target host killing functions may be found by structural homology, or by evaluating entities found in characteristic gene organization motifs. Plasmid, phage receptor, or host cell recognition genes are typically found in particular gene arrangements, and other entities found in the corresponding arrangements can be found by evaluating available sequence information, e.g., by bioinformatics means. These may also serve as the starting points to screen for variants of the structures, e.g., mutagenizing such structures and screening for those which have desired characteristics, e.g., broader plasmid transmissibility, broader phage receptor function, or wider host target specificity. Standard methods of mutagenesis may be used. Gene or domain shuffling technologies may be applicable to find appropriate variants.

Plasmid host cell compatibility, phage receptor segments, or phage killing functions may be similarly identified, and prevalent or specific target motifs may be identified for optimization for the methods described. Many of those targets may be highly expressed proteins, carbohydrate, or lipid containing structures found on the various potential target strains. Pili structures found on the outside of the bacterial cell may be another structure for which proteins target for binding. Mutagenesis may broaden binding selectivity or increase stability of segments or the entire construct, deletion strategies may eliminate extraneous segments.

The components of the Gram-positive bacteria cell wall may be shared with components of the Gram-negative cell wall, or possibly with other mycobacteria or spores. However, there may be additional layers of wall in the Gram negative which may also serve as additional barriers to phage access. Other activities derived from phage or elsewhere may be combined to penetrate the more complex Gram-negative cell wall structures. In particular, multiple catalytic segments may provide multiple activities, which may function synergistically, within a single construct, or which can provide synergistic effect when combined with another therapeutic, e.g., antibiotic or antimicrobial.

A targeting moiety may increase the local concentration of a catalytic fragment, but a linker of appropriate length may also increase the number of wall degrading events locally. Thus, linkers compatible with the target and catalytic motifs or of appropriate length may be useful and increase the catalytic penetration activity leading to stasis or killing of target bacteria.

One of skill would recognize that certain modifications can be made to the catalytic or functional domains of the polypeptide without diminishing their biological activity. Some modifications may be made to facilitate the cloning, expression, or incorporation of the catalytic domain into a fusion polypeptide. Such modifications are well known to those of skill in the art and include, for example, the addition of codons at either terminus of the polynucleotide that encodes the catalytic domain, e.g., a methionine added at the amino terminus to provide an initiation site, or additional amino acids (e.g., poly His) placed on either terminus to create conveniently located restriction enzyme sites or termination codons or purification sequences.

It must be noted that as used herein and in the appended claims, the singular forms "a", "and", and "the" include plural referents unless the context clearly dictates otherwise. Thus, e.g., reference to "a bacteriophage" includes a plurality of such bacteriophage and reference to a "host bacterium" includes reference to one or more host bacteria and equivalents thereof known to those skilled in the art, and so forth.

Publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. Citations are incorporated herein by reference in their entirety.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

EXAMPLES

Example 1: F Factor Conjugation

Important parameters which should be optimized for conjugation conditions for a specific plasmid and host include, e.g., logarithmic phase of the donor and recipient cells, incubation temperature for conjugation, and other conditions. Thus, various components which may affect conjugation frequency or efficiency may include temperature, and may be titrated across the appropriate range. For therapeutic use for warm blooded animals, probably between about 25-45 degrees C., while for environmental situations, the temperature range may be a range of perhaps 20 degrees above or below ambient temperature. Aspects of mixing, agitation, ionic strength, ion concentration, and the like may also be optimized. Optimization will be tested for molar relationship of F+ to F− hosts and the like.

In certain situations, conjugation may not require actual expression of pili or such structures. Conjugation may be dependent upon other "conjugation related" biology, and there may be alternative features in the process which may not be pilus dependent. This can be investigated using current technology and methods.

Example 2: Transfer Plasmids/Convert Cells from F− to F+

The demonstration of conversion of F− hosts to F+ hosts can be shown using standard conjugation experiments. See, e.g.; Paranchych and Frost (1988) "The Physiology and Biochemistry of Pili" *Advances in Microbial Physiology* 29:53-114; Low and Porter (1978) "Modes of Gene Transfer and Recombination in Bacteria" *Ann. Rev. Genetics* 12: 249-287; Rowbury (1977) "Bacterial Plasmids with Particular Reference to their Replication and Transfer Properties" *Progress in Biophysics & Molecular Biology* 31: 271-317; Simon, et al. (1983) "A Broad Host Range Mobilization System for In Vivo Genetic Engineering: Transposon Mutagenesis in Gram Negative Bacteria". *Nature Biotechnology* 1: 784-791; Clewell, et al (1993). *Bacterial Conjugation*. Plenum Press, New York. ISBN 0-306-44376-7; Grohmann, et al. (2003). "Conjugative Plasmid Transfer in Gram-Positive Bacteria". *Microbiology and Molecular Biology Reviews* 67(2):277-301. Efficiencies, transfer rates, optimization of conditions for particular plasmids and hosts, and the like can be evaluated.

For example, the methodology may follow along the lines of growing a volume, e.g., 5 ml, of donor and recipient cells to OD 0.5-0.7. From these cultures, mix a small volume, e.g., 100 microliters of donor and recipient cultures. (Controls: 100 microliters of donor and recipient cells alone). Typically, there is a wash by centrifuging and washing, e.g., with 0.85% saline twice. The pellet is resuspended, e.g., in 20 microliters of saline, and spot on a well-dried Petri plate, e.g., LB. The plate is allowed to dry and incubated overnight, e.g., at 30 degrees.

After the growth period, the culture is scraped into medium, e.g., 500 microliters saline, vortexed to disrupt mating pairs. The suspension is plated at various appropriate dilutions on respective selection plates, e.g., dual antibiotic plates. Alternatively, detectable markers (GFP or the like) may be used to avoid use of antibiotics. Appropriate colonies are typically confirmed for conjugation, e.g., with PCR for the presence of conjugative plasmid.

Example 3: Marker Incorporated into Plasmid

An appropriate marker is selected, which is preferably easily detected. While virulence or resistance markers will generally be of most interest in the therapeutic or public health embodiments, easier detection markers will be useful in establishing that the methodology does work. Thus, a fluorescent marker, e.g., GFP, can be used to show that the marker does get transferred at a detectable, and optimized for the desired system.

The marker is PCR amplified and cloned into a suitable restriction site into a plasmid. The rate and optimum conditions for efficient transfer among the plasmids and hosts of interest may be determined. These may include aspects of the plasmid, transfection conditions, conjugation conditions, kinetics, temperature, and the like. Evaluation of rates of uptake and expression may make use, e.g., of fluorescent activated cell sorting or similar methodologies.

Example 4: Selection; Elimination of Cells Lacking Marker

To select cells that have acquired the plasmid, using an antibiotic or other selectable marker on the plasmid would be ideal since plating the cells on an antibiotic plate would select only those cells that have acquired the plasmid. The selection marker may be linked to the desired marker so the selection conditions will preferably select nearly directly for the marker. If the marker is targetable, e.g., by phage, the cells which have survived the selection should be susceptible to the phage infection process mediated by the receptor.

Example 5: Linking Phage Receptor Marker to Selection Marker

The phage receptor encoding genes and the selection marker would be on the same plasmid and preferably closely linked. Means may be incorporated to minimize the likelihood that the receptor encoding genes and the marker cannot easily be separated. These markers may be closely linked to the origin of replication of the appropriate plasmid.

Example 6: Deletion of Extraneous Sequence from F Factors

Methods may be applied towards identifying the receptor encoding region on the plasmid containing phage susceptibility by generating individual gene deletion mutants and testing for tectivirus susceptibility. With methods of molecular biology, sequencing and bioinformatics analysis, and manipulation methods, regions of the plasmid can be identified to see which are necessary for the functional transfer of phage susceptibility.

The identified regions may be further evaluated by complementing mutated gene products in trans and testing for tectivirus susceptibility. Thereafter, methods can be used to remove extraneous portions of the plasmid to obtain only the receptor encoding region linked to critical plasmid conjugation segments.

Example 7: Various Selection Markers

Beta galactosidase, luciferase, GFP, ampicillin, kanamycin, chloramphenicol, tetracycline, streptomycin, etc. will be good selection markers for these strategies. The selection or detection means are well known and readily available.

Example 8: Transfer of Conjugative Plasmid from a Salmonella Bacterial Cell to a Xanthomonas Bacterial Cell Five milliliter cultures of donor bacteria (*S. typhimurium* LT2 (pLM2) obtained from Felix d'Hérelle Reference Center for Bacterial Viruses, Laval, Canada) and recipient bacteria (*X. campestris* HER1103, obtained from Felix De Herelle Center, Laval, Canada) were grown in LB broth at 37° C. and 30° C. with shaking at 200 rpm. Final OD600 of the cultures was between 0.5-0.7.

One hundred microliters of donor and recipient cultures were mixed together. Control samples were also prepared: one hundred microliters of donor cells only and one hundred microliters of recipient cells only. Cells were pelleted by centrifugation and washed twice with 0.85% saline solution. Pellets were resuspended in twenty microliters of saline solution and spotted on a well-dried LB plate. The plate was allowed to air dry and was then incubated at 30° C. overnight.

The following day cultures were scraped into 500 microliters saline solution. Mating pairs were separated by vortexing. Five hundred additional microliters of saline solution was added. Undiluted and diluted serially diluted samples were plated onto dual antibiotic plates. i.e., LB with kanamycin 25 µg/ml and streptomycin 100 µg/ml. Because *S. typhimurium* LT2 (pLM20) is kanamycin resistant and *X. campestris* HER1103 is streptomycin resistant, only *X. campestris* HER1103 cells that have received the pLM2 plasmid and kanamycin resistance gene grow on the dual antibiotic plates. PCR was used to screen bacteria that grow on the dual antibiotic plates for the presence of the conjugative plasmid. Plasmid specific oligonucleotide primers were used for the screening. Single colonies of *X. campestris* cells transfected with the conjugative plasmid were inoculated into LB broth containing the kanamycin and streptomycin and are grown at 30° C. with shaking at 200 rpm to a final OD600 between 0.5-0.7. A lawn of bacteria was plated on an LB plate and 2 microliters of PRD1 phage was spotted onto the bacterial lawn. The plates were incubated at 30° C. overnight and the presence of viral plaques, indicating death or reduced growth of the plasmid-containing bacteria after infection by the PRD1 phage, was confirmed the next day.

Example 9: Pairing of Various Plasmids with Appropriate Phage

The above description provides teachings of exemplary plasmid dependent phage types, and specific examples of phage within those categories. Various target species are described, and some of the plasmids are species specific or somewhat less specific (perhaps clusters of related species). Appropriate plasmids may be introduced into a target specie, whether by conjugation or other methodology, including transformation or electroporation. Once the plasmid is internalized and appropriate conditions found where expression occurs, the phage susceptibility is easily tested by standard methods. The assays may often be in liquid or plate cultures, as appropriate for the desired evaluations. Thus, testing of various plasmid types, e.g., IncD plasmids with Phage D, and others can be confirmed or screened as new pairings are reported or tested. Culture conditions which improve the expression of desired receptors or efficiency of phage effects can be screened.

What is claimed is:

1. A method for reducing the number of a recipient bacterial population comprising the steps of:
   (a) transferring a conjugative plasmid from a donor bacterial population to the recipient bacterial population, wherein the conjugative plasmid is selected from the group consisting of Inc group N, P, W, D, M, X, P1, U, C, or J; wherein the transferring comprises contacting the donor bacterial population with the recipient bacterial population, and wherein the recipient bacterial population is not susceptible to binding by a phage until the recipient bacterial population expresses a phage receptor expressed by the conjugative plasmid; and
   (b) contacting the recipient bacterial population with the phage that binds to the phage receptor, wherein said contacting localizes the phage to recipient bacteria expressing the phage receptor, thereby reducing the number of the recipient bacterial population.

2. The method of claim 1, wherein the plasmid comprises a recombinant expression cassette comprising a strong promoter functional in the recipient bacterial population operably linked to a sequence encoding the phage receptor.

3. The method of claim 1, wherein the plasmid is selected from the group consisting of:

Inc group N, P, and W.

4. The method of claim 1, wherein the phage is selected from the group consisting of Tectiviridae, Inoviridae, Leviviridae, Siphoviridae, filamentous phage, and RNA phage.

5. The method of claim 1, wherein the conjugative plasmid is modified.

6. The method of claim 1, wherein the donor bacterial population comprises bacteria from at least one genus selected from the group consisting of:

*Escherichia, Pseudomonas, Salmonella, Proteus, Vibrio, Acinetobacter, Bacillus*, and *Micrococcus*.

7. The method of claim 1, wherein the recipient bacterial population comprises bacteria from at least one genus selected from the group consisting of:

*Escherichia, Pseudomonas, Salmonella, Proteus, Vibrio, Acinetobacter, Bacillus*, and *Micrococcus*.

8. The method of claim 1, wherein the method is carried out in vitro.

9. The method of claim 1, wherein the recipient bacterial population is killed by the phage.

* * * * *